United States Patent
Popovtzer et al.

(10) Patent No.: US 10,478,132 B2
(45) Date of Patent: Nov. 19, 2019

(54) GLUCOSE CONJUGATED GOLD NANOPARTICLE

(71) Applicant: Bar-Ilan University, Ramat Gan (IL)

(72) Inventors: Rachela Popovtzer, Givat Shmuel (IL); Menachem Motiei, Ashdod (IL); Tamar Dreifuss, Lod (IL)

(73) Assignee: BAR-ILAN UNIVERSITY, Ramat Gan (IL)

(*) Notice: Subject to any disclaimer, the term of this patent is extended or adjusted under 35 U.S.C. 154(b) by 0 days.

(21) Appl. No.: 15/396,881

(22) Filed: Jan. 3, 2017

(65) Prior Publication Data
US 2017/0189560 A1 Jul. 6, 2017

Related U.S. Application Data

(60) Provisional application No. 62/274,309, filed on Jan. 3, 2016.

(51) Int. Cl.
*A61K 9/51* (2006.01)
*A61B 5/00* (2006.01)

(52) U.S. Cl.
CPC .................. *A61B 5/7282* (2013.01)

(58) Field of Classification Search
CPC . A61B 5/064; A61K 9/14; A61K 9/16; A61K 9/1611; A61K 9/1617; A61K 9/1623; A61K 9/1641; A61K 9/167; A61K 9/51; A61K 9/5107; A61K 9/5161
See application file for complete search history.

(56) References Cited

U.S. PATENT DOCUMENTS

| | | | |
|---|---|---|---|
| 9,107,895 B2 | 8/2015 | Aydogan et al. | |
| 2005/0020869 A1 | 1/2005 | Hainfeld et al. | |
| 2011/0020243 A1* | 1/2011 | Aydogan | A61K 31/7004 424/9.42 |
| 2011/0110868 A1* | 5/2011 | Akhtari | A61K 49/085 424/9.322 |

OTHER PUBLICATIONS

Rinat Meir et al., "Nanomedicine for Cancer Immunotherapy: Tracking Cancer-Specific T Cells in Vivo with Gold Nanoparticles and CT Imaging", Acsnano, vol. 9, No. 6, p. 6363-6372, 2015.

* cited by examiner

*Primary Examiner* — Micah Paul Young
(74) *Attorney, Agent, or Firm* — The Roy Gross Law Firm, LLC; Roy Gross

(57) ABSTRACT

Composition methods and kits for diagnosing and treating tumors within a subject. The compositions disclosed comprise: a gold nanoparticle; PEG or derivatives thereof, wherein said PEG or derivatives thereof have a molecular weight of 400 to 1500 Dalton; and a 2-Deoxy-D-glucose, wherein the PEG or derivatives thereof are linked to the gold nanoparticle and to said 2-Deoxy-D-Glucose, and wherein the 2-Deoxy-D-Glucose is linked to the PEG or derivatives thereof at the 2-Carbon position of the 2-Deoxy-D-Glucose.

18 Claims, 14 Drawing Sheets

(10 of 14 Drawing Sheet(s) Filed in Color)

GLUCOSE CONJUGATED GOLD NANOPARTICLE

CROSS-REFERENCE TO RELATED APPLICATIONS

This application claims the benefit of U.S. Provisional Patent Application No. 62/274,309, filed Jan. 3, 2016, and entitled "GLUCOSE CONJUGATED GOLD NANOPARTICLE", the content of which is incorporated herein by reference in its entirety.

FIELD OF INVENTION

The present invention relates to the field of nanoparticles and their therapeutic and diagnostic use for various health related conditions.

BACKGROUND OF THE INVENTION

Gold particles are one of the most widely used classes of nanomaterials for chemical, bioanalytical, biomedical, optical and nano-technological applications. Gold nanoparticles can be manufactured in a variety of methods. As a non-limiting example, synthesis of substantially spherical gold nanoparticles that are covered with negatively charged citrate ions can be prepared by using sodium citrate to reduce tetrachloroaurate (HAuCl4 has previously described by Enustun & Turkevich (Enustun, & Turkevich, Journal of the American Chemical Society 1963: 85, 3317-3328).

Cancer detection is based on both structural and functional imaging techniques. Structural techniques (e.g., US, MM and CT) identify anatomic details and provide information on tumor location, size and spread, based on endogenous tissue contrast. However, they are not sufficiently sensitive for detecting critically small tumors or metastases since they lack structural manifestation. The development of the main clinically applicable functional imaging technique, positron emission tomography (PET) using the glucose analog 18F-2-fluoro-2-deoxy-d-glucose ([$^{18}$F]FDG) has eventually revolutionized the field of medical oncology. [$^{18}$F]FDG-PET is based on the increased metabolic profile of malignant cells and provides the ability to discern molecular and cellular alterations associated with pathological conditions, even before structural modifications occur. However, [$^{18}$F]FDG-PET lacks anatomical information, and thus necessitates the incorporation of an additional structural imaging modality such as CT or MM in order to obtain an accurate anatomic localization of the foci of increased metabolic activity. The combination of PET with CT (PET-CT) enables both functional and anatomical information in a single setting. However, in view of the relatively high cost of PET scans, the dependence on the short-lived [$^{18}$F]FDG (T1/2<2 h) and its non-specificity for cancer which leads to high rate of false positives (glucose uptake is not cancer-specific), the development of a single modality which will overcome these drawbacks is highly desirable.

Although glucose-conjugated gold nanoparticles have been previously reported as contrast agents to image tumors using techniques such as CT or X-ray imaging (US. Pub. No. 9107895), the efficiency of such conjugates remained inadequate. Therefore, the need for an efficient glucose-conjugated gold nanoparticle for CT or X-ray imaging remained.

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

According to a first aspect, the invention provides a composition comprising: a gold nanoparticle; PEG or derivatives thereof, wherein the PEG and derivatives thereof have a molecular weight of 400 to 1500 Dalton; and a 2-Deoxy-D-glucose, wherein the PEG or derivatives thereof are linked to the gold nanoparticle and to the 2-Deoxy-D-Glucose, and wherein the 2-Deoxy-D-Glucose is linked to said PEG and derivatives thereof at the 2-Carbon position of said 2-Deoxy-D-Glucose.

In some embodiments, the gold has a concentration of 30 to 60 milligrams/milliliter (mg/ml). In some embodiments, the 2-Deoxy-D-Glucose is covalently linked to the PEG. In some embodiments, the PEG or derivatives thereof are linked to the gold nanoparticle via a chemical attachment selected from the group consisting of: covalent attachment, semi-covalent attachment and non-covalent attachment.

In some embodiments, the PEG or derivatives thereof comprise one or more functional groups selected from the group consisting of: mercapto group, carboxyl group, mercaptoethyl, carboxyethyl, hydroxyl, amine, imide, sulfone, disulfide, and NHS esters.

In some embodiments, the gold nanoparticle is linked to 4,000-20,000 molecules of said PEGs or derivative thereof. In some embodiments, the gold nanoparticle is linked to 4,000-20,000 molecules of said 2-deoxy-D-glucose.

In some embodiments, the gold nanoparticle has a diameter of 10 to 40 nanometers. In some embodiments, composition has a diameter of 20 to 60 nanometers.

In some embodiments, the composition further comprises a drug. In some embodiments, the drug is an anti-cancer therapeutic agent.

According to another aspect, the invention provides a method of imaging a tumor comprising: administering to a subject a composition comprising: a gold nanoparticle; PEG or derivatives thereof, wherein said PEG and derivatives thereof have a molecular weight of 400 to 1500 Dalton; and a 2-Deoxy-D-glucose, wherein the PEG or derivatives thereof are linked to the gold nanoparticle and to the 2-Deoxy-D-Glucose, wherein the 2-Deoxy-D-Glucose is linked to the PEG and derivatives thereof at the 2-Carbon position of the 2-Deoxy-D-Glucose, and wherein the composition penetrates to and accumulates in tumor cells; and scanning the subject or a portion thereof using a diagnostic imaging technique, thereby imaging the tumor cells. In some embodiments, the diagnostic imaging technique is selected from the group consisting: computed X-ray tomography (CT), ultrasound (US) and magnetic resonance imaging (MRI).

In some embodiments, the administering is by an intravenous injection. In some embodiments, the scanning is performed 0.5 to 24 hours post said administering.

In some embodiments, the subject is a human subject. In some embodiments, the subject is at risk of being afflicted with cancer.

In some embodiments of the method disclosed, the composition further comprises a drug. In some embodiments, the drug is an anti-cancer therapeutic agent. In some embodiments, the drug is activated within said tumor cells.

In some embodiments, the method further comprises a step of directing an ionizing irradiation to the composition thereby obtaining locally enhanced radiation therapy within the tumor cells.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
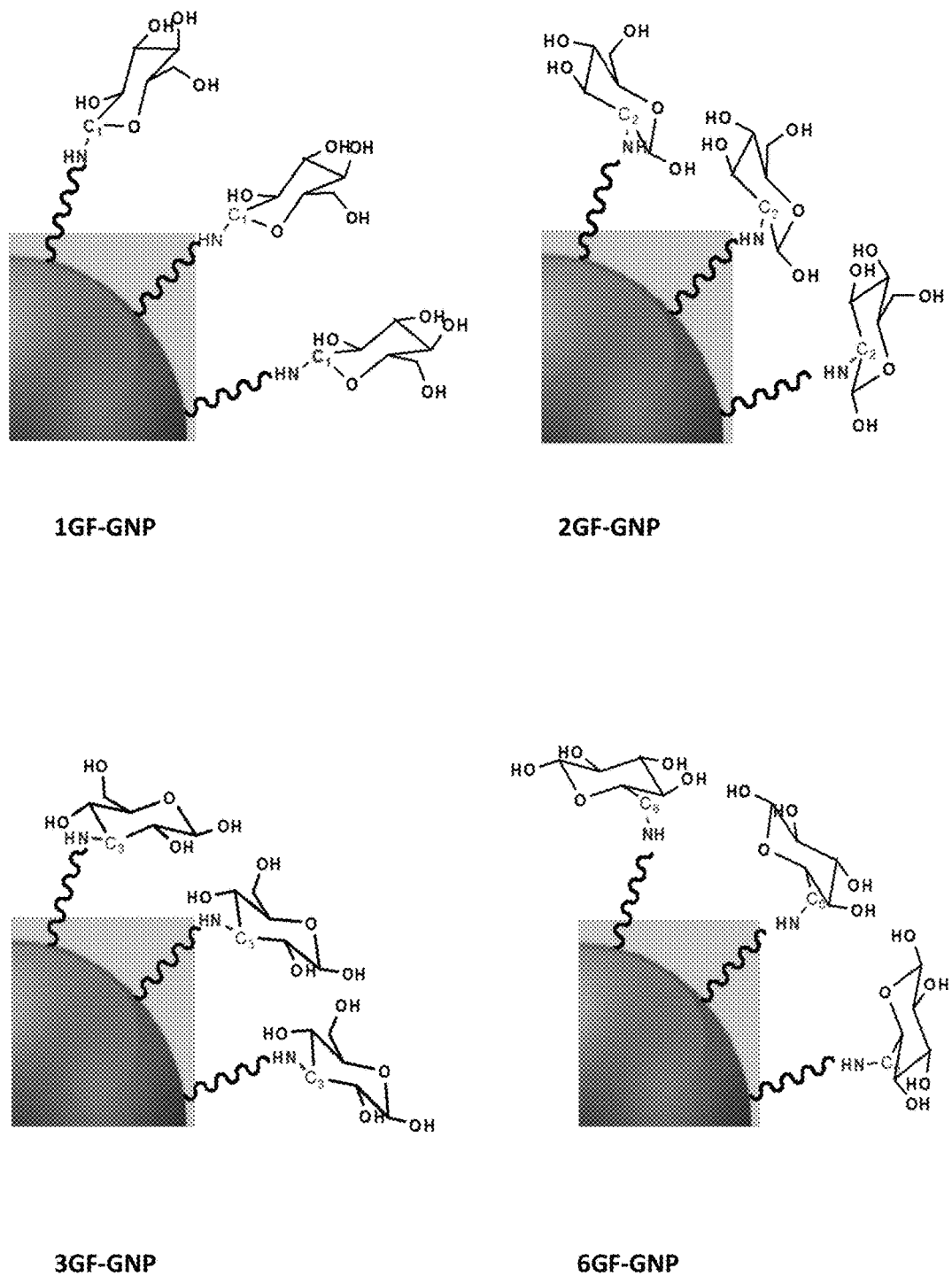
FIG. 1 is schematic presentations of the four distinct GF-GNPs, with the same shape and size, differing only in the intra-molecular glucose conjugation site ($C_1$, $C_2$, $C_3$, and $C_6$)

The present invention, in some embodiments, provides a composition comprising a nanoparticle conjugated to 2-Deoxy-D-glucose through its 2' carbon position via a linker selected from poly ethylene glycol (PEG) or derivatives thereof having a molecular weight of 400 to 1500 Dalton. In some embodiments, the composition is internalized by and accumulates in tumor cells/cancer cells in vitro. In some embodiments, the composition is internalized by and accumulates in tumor cells/cancer cells in vivo. In some embodiments, the internalization and accumulation of the composition in vivo is specific to cancer cells or significantly higher in cancer cells than non-cancer cells. In some embodiments, accumulation of the composition in tumor cells/cancer cell allows imaging of these cells such as by performing computed X-ray tomography (CT) scan. In some embodiments, the composition accumulates in vivo in cells of a tumor rather than in cells of an inflamed tissue, therefore allows the distinction between cancer and inflammatory processes.

The present invention is based in part on the surprising finding that the composition of the invention exhibits significantly increased uptake by cancer cells in vivo and accumulation therein over other nanoparticle conjugated to glucose either directly or via a linker (e.g., mercaptosuccinic acid).

As exemplified in the example section, and without wishing to be bound by any mechanism of action, the composition of the invention may be recognized by GLUT-1. As further exemplified the composition of the invention may be internalized into the cell by endocytosis. As used herein the terms "GLUT-1" and "glucose transporter 1" refer to a membrane proteins that facilitates the transport of glucose over a plasma membrane.

In some embodiments, the compositions of the invention enhance image contrast during diagnostic imaging. The term "diagnostic medical imaging", or simply "medical imaging" or "diagnostic imaging" refers to a method of graphically or pictorially investigating an animal or human body for the purposes of studying the body's anatomy or physiology or an abnormality thereof. Typical methods of medical imaging which are contemplated by the present invention include, among others, computed X-ray tomography (CT), ultrasound (US), magnetic resonance imaging (MRI), and optical imaging.

As used herein, the terms "tumor cells" and "cancer cells" are used interchangeably to refer to cells characterized by unregulated cell growth. In some embodiments, the tumor/cancer cells are glucose transporter overexpressing cells (e.g., GLUT1 overexpression).

The term "tumor" as used herein encompasses both primary and metastasized solid tumors and carcinomas of any tissue in a subject, including, but not limited to breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). The term "tumor" also encompasses solid tumors arising from hematopoietic malignancies such as leukemia, including chloromas, plasmacytomas, plaques and tumors of mycosis fungoids and cutaneous T-cell lymphoma/leukemia, and lymphomas including both Hodgkin's and non-Hodgkin's lymphomas. The term "tumor" also encompasses radio resistant and/or chemo resistant tumors, including, but not limited to radio resistant and/or chemo resistant variants of any of the tumor listed above.

In some embodiments, cancer cells are squamous carcinoma cells.

As used herein, the term "inflamed tissue" includes tissues that have elevated inflammatory response cells infiltrates. Inflamed tissue may be characterized by one or more of the following: (1) dilation of capillaries to increase blood flow to the affected area; (2) changes in the microvasculature structure, leading to the escape of inflammatory response cells from circulation; and/or (3) inflammatory response cells migrating from the capillaries and accumulating at the site of inflammation.

In some embodiments, as exemplified in the examples section, in vivo and/or in vitro accumulation of the composition in tumor cells is significantly higher than that of a similar composition in which the 2-deoxy-D-glucose is substituted by other glucose molecules, or in which the 2-deoxy-D-glucose is attached to the PEG at a position other than its 2' carbon position. For a non-limiting example, a position other than 2 carbon position includes 1-Carbon, 3-Carbon, or other such positions.

"Other glucose molecules", as used herein, include any derivative of glucose in which the hydroxyl group at position 2 was not replaced, such as for a non-limiting example: L-glucose, D-glucose, 1-deoxy-D-glucose, 3-deoxy-D-glucose, 4-deoxy-D-glucose, 6-deoxy-D-glucose or other derivatives thereof.

As used herein the term "in vivo" refers to any process/event that occurs within a living subject. As used herein the term "in vitro" refers to any process/event that occurs outside a living subject in an artificial environment, such as in cell culture. In some embodiment, in vitro refers to cell lines grown in cell culture. In some embodiment, in vitro refers to tumor cells grown in cell culture.

In some embodiments, as further exemplified in the examples section, in vivo and/or in vitro accumulation of the composition by tumor cells is significantly higher than that of a similar composition in which the PEG or derivatives thereof are substituted with PEG or derivatives thereof having a molecular weight lower than 400 Da or higher than 1500 Da. In some embodiments, as further exemplified in the examples section, accumulation of the composition in tumor cells is significantly higher than that of a similar composition in which the 2-deoxy-D-glucose is substituted by other glucose molecules and the PEG or derivatives thereof are substituted with PEG or derivatives thereof having a molecular weight lower than 400 Da or higher than 1500 Da.

As used herein "significantly higher" is at least 1.5 folds, or alternatively at least 2 folds, or alternatively at least 3 folds, or alternatively at least 4 folds, or alternatively at least 5 folds, or alternatively at least 10 folds higher. Each possibility represents a separate embodiment of the present invention.

A "similar composition", as used herein, differ from the compositions of the invention only by substitution of a component as described (e.g., substitution of 2-deoxy-D-glucose with other glucose molecules, substitution of PEG or derivatives thereof having a molecular weight of 400 to 1500 Da with other PEG or derivatives thereof having a molecular weight lower than 400 Da or higher than 1500 Da).

The Composition

According to a first aspect, the invention provides a composition comprising: a nanoparticle; poly ethylene glycol (PEG) or derivatives thereof; and a 2-Deoxy-D-glucose, wherein the PEG or derivatives thereof are linked to the gold nanoparticle and to the 2-Deoxy-D-Glucose, and wherein the 2-Deoxy-D-Glucose is linked to the PEG and derivatives thereof at the 2-Carbon position of the 2-Deoxy-D-Glucose.

In some embodiments, the nanoparticle is a magnetic nanoparticle. Any magnetic nanoparticle suitable for use for imaging by magnetic resonance imaging (MRI) may be used in the composition and methods of the present disclosure. The magnetic particle may be formed, at least in part, from any material affected by a magnetic field. Examples of suitable materials include, but are not limited to: magnetite, hematite, ferrites, and materials comprising one or more of iron, cobalt, manganese, nickel, chromium, gadolinium, neodymium, dysprosium, samarium, erbium, iron carbide, iron, or a combination thereof. In some embodiments, the nanoparticle is a metal nanoparticle. Any metal and/or combination of metals suitable for use for imaging by CT or X-ray may be used in the composition and methods of the present disclosure. In some embodiments, metals which can be used to form the nanoparticle of the invention are heavy metals, or metal with a high Z number. Examples of suitable metals include, but are not limited to: gold, silver, platinum, palladium, cobalt, iron, copper, tin, tantalum, vanadium, molybdenum, tungsten, osmium, iridium, rhenium, hafnium, thallium, lead, bismuth, gadolinium, dysprosium, holmium, and uranium, or a combination thereof. In some embodiments, the nanoparticle is a gold (Au) nanoparticle.

A "gold nanoparticle" as used herein refers to a particle of gold (Au) having a particle size on the nanometer (nm) scale, generally less than 1 micrometer. In some embodiments, the nanoparticle has a particle size up to 100 nm, or alternatively up to 50 nm, or alternatively up to 40 nm, or alternatively up to 35 nm, or alternatively up to 30 nm, or alternatively up to 25 nm, or alternatively up to 20 nm. In other embodiments, the nanoparticle has a particle size greater than 5 nm, or alternatively greater than 10 nm, or alternatively greater than 20 nm, or alternatively greater than 30 nm, or alternatively greater than 35 nm, or alternatively greater than 40 nm. Each possibility represents a separate embodiment of the present invention.

In some embodiments, the gold (Au) concentration of the composition is 30 to 60 milligrams/milliliter (mg/ml). In some embodiments, the gold (Au) concentration of the composition is 20 to 70, or alternatively 30 to 60, or alternatively 30 to 50, or alternatively 40 to 60 mg/ml.

The composition of the invention comprising a gold nanoparticle attached to 2-Deoxy-D-Glucose via PEG and derivatives thereof has a mean hydrodynamic diameter, as measured by dynamic light scattering techniques, of less than 100 nm, less than 80 nm, less than 60 nm, between 5 to 100 nm, between 10 to 90 nm, between 10 to 80 nm, between 10 to 70 nm, between 10 to 60 nm, between 20 to 60 nm, between 30 to 60 nm. Each possibility represents a separate embodiment of the present invention. The composition of the invention comprising a gold nanoparticle attached to 2-Deoxy-D-Glucose via PEG and derivatives thereof has a mean hydrodynamic diameter, as measured by dynamic light scattering techniques, of between 10 and 60 nm.

As used herein, the term "diameter" refers to the largest linear distance between two points on the surface of a described particle/composition (e.g., gold nanoparticle, gold nanoparticle attached to 2-Deoxy-D-Glucose via PEG and derivatives thereof). The term "diameter", as used herein, encompasses diameters of spherical particles/compositions as well as of non-spherical particles/compositions.

The term Polyethylene glycol (PEG) is used herein to refer to a condensation polymer of ethylene oxide (molecular weight 62 Da) and water with general formula HO—$(CH_2$—$CH_2$—$O)_n$—H. The low molecular weight members from n=2 to n=4 are diethylene glycol (molecular weight 106 Da), triethylene glycol (molecular weight 150 Da) and tetraethylene glycol (molecular weight 194 Da) respectively, which are produced as pure compounds. Where appropriate, the abbreviation (PEG) is used in combination with a numeric suffix which indicates the average molecular weight of the PEG. A form of PEG or a PEG species is a PEG or PEG derivative with a specified average molecular weight.

In some embodiments, the PEG or derivative thereof of the instant invention have a molecular weight of 300 to 3,000 Dalton, or alternatively 300 to 2,500 Dalton, or alternatively 300 to 2,000 Dalton, or alternatively 300 to 1,800 Dalton, or alternatively 300 to 1,500 Dalton, or alternatively 400 to 3,000 Dalton, or alternatively 400 to 2,500 Dalton, or alternatively 400 to 2,000 Dalton, or alternatively 400 to 1,800 Dalton, or alternatively 400 to 1,500 Dalton, or alternatively 500 to 1,400 Dalton, or alternatively 600 to 1,300 Dalton. In some embodiments, the PEG or derivative thereof of the instant invention have a molecular weight of 400 to 1,500 Dalton.

As used herein "PEG or derivatives thereof" refers to any compound including at least one polyethylene glycol moiety. PEG polymers exist in linear forms, branched forms and/or multi-arm polyethylene glycols. The term "PEG derivative", as used herein, relates to PEG which is modified by the addition of one or more straight chain or branched C1-C6 alkyl groups. A PEG may further comprise a functional group. PEG molecules may be mono-, di-, or multi-functional polyethylene glycols. Exemplary functional groups include, but are not limited to, the following: a hydroxyl, a carboxyl, an amino, a phosphate, a phosphonate, a sulfate, asulfite, a sulfenate, a sulfonate, a sulfoxide, a sulfone, an amide, an ester, a ketone, an aldehyde, a nitrile, an alkene, an alkyne, an ether, a thiol (or mercapto), a hydroxyamic acid, a silane, a silicate, a carbamodithionate, a dithionate, a mercaptan, a disulfide, a peroxide and a nitronate group. In some embodiments, a PEG derivative comprises one or more groups selected from the group consisting of: acid (carbonic acid, sulphonic acid), aldehyde, COOH (carboxyl group), CHO, $OCH_3$ (methoxyl), CN, OH (hydroxyl group), OR, SH (thiol group/mercapto group), succinimidyl ester (NHS), SR, N3, NH2 (amine group) or NHR, wherein R=C1 to C4 chain.

In some embodiments, PEG derivatives comprise one or more functional groups selected from the group consisting of: mercapto, carboxyl, mercaptoethyl, carboxyethyl, hydroxyl, amine, imide, sulfone, disulfide, and NHS esters.

In a non-limiting example of the instant invention a PEG derivative may be O-(2-Carboxyethyl)-O'-(2-mercaptoethyl) heptaethylene glycol.

The terms "2-deoxy-D-glucose" and "2-DG" are used interchangeably herein to refer to a glucose molecule in which the 2-hydroxyl group is replaced by hydrogen, so that it cannot undergo further glycolysis and derivative and analogue thereof. Typically, 2-deoxy-D-glucose is taken up by glucose transporters of the cell, therefore, cells with higher glucose uptake, for example tumor cells, have also a higher uptake of 2-DG. As used herein, the term "analogue" refers to a chemical compound with a structure and function similar to that of a reference compound but differing from it in respect to a particular component, functional group, atom, etc. As used herein, a 2-DG analog is any D-glucose analog other than 2-DG that does not have a hydroxyl group at the 2 position of the glucose ring. An analog of glucose or 2-DG can have a fluorine in place of a hydrogen at any position on the glucose ring; thus, 2-fluoro-2-deoxy-D-glucose (2-FDG) and 2-difluoro-2-deoxy-D-glucose are 2-DG analogs. An analog of 2-DG can have an amino group in place of a hydroxyl group at any position on the glucose ring other than the 6 position; thus, 2-amino-2-deoxy-D-glucose (2-glucosamine) and 2-amino-2-deoxy-D-galactose (2-galactosamine) are 2-DG analogs. Other illustrative 2-DG analogs include 2-F-mannose, 2-mannosamine, 2-deoxygalactose, 2-F-deoxygalactose, and di, tri, and other oligosaccharides that contain one or more of the preceding or following 2-DG analogs. Analogs are commercially available and/or can be synthesized by one of skill in the art using routine techniques with reference to the scientific literature.

In some embodiments, the PEG or derivatives thereof are chemically linked/attached to the gold nanoparticle of the composition of the invention. In some embodiments, the PEG or derivatives thereof are linked to the gold nanoparticle via a chemical attachment selected from the group consisting of: covalent attachment, semi-covalent attachment and non-covalent attachment. In some embodiments, the PEG or derivatives thereof are covalently attached to the gold nanoparticle. In some embodiments, the PEG or derivatives thereof are semi-covalently attached to the gold nanoparticle. Alternatively, or additionally the PEG or derivatives thereof are non-covalently attached to the gold nanoparticle.

In some embodiments, the 2-Deoxy-D-Glucose is chemically linked to the PEG and derivatives thereof at the 2-Carbon position of the 2-Deoxy-D-Glucose. In some embodiments, the 2-Deoxy-D-Glucose is covalently linked to the PEG and derivatives thereof at the 2-Carbon position of the 2-Deoxy-D-Glucose.

As used herein, the term "chemically linked" is understood to mean connected by an attractive force between atoms strong enough to allow the combined aggregate to function as a unit. This includes, but is not limited to, chemical bonds such as covalent bonds, non-covalent bonds such as ionic bonds, metallic bonds, and bridge bonds, hydrophobic interactions, hydrogen bonds, and van der Waals interactions.

As used herein, the term "covalent attachment", "covalently attached", "covalently linked" and "covalently bonded" refer to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers attached covalently to a surface can also be bonded via means in addition to covalent attachment.

As used herein, the term "semi-covalent attachment" and "dative covalent bond" refers to a co-ordinate bond wherein the shared pair of electrons which form the bond come from the same atom. In the present disclosure, the dative covalent bond may occur between the metal, e.g. gold, and sulfur group.

In some embodiments, the invention provides a gold nanoparticle linked to 4000-20000 PEGs or derivative thereof, and each PEG is chemically linked to one 2 deoxy-D-glucose molecule at the 2-Carbon position of the 2-Deoxy-D-Glucose. In some embodiments, the gold nanoparticle is linked to 1000-50000 PEGs, or alternatively –200040000 PEGs, or alternatively –300030000 PEGs, or alternatively 4000-20000 PEGs, or alternatively 5000-10000 PEGs.

In some embodiments, the invention provides a plurality of gold nanoparticles, each is linked to 4000-20000 PEGs or derivative thereof, and to 4000-20000 molecules of 2-Deoxy-D-Glucose, wherein each molecule of PEG is linked to one molecule of the 2-Deoxy-D-Glucose, and wherein the 2-Deoxy-D-Glucose is linked to the PEG or derivatives thereof at the 2-Carbon position of the 2-Deoxy-D-Glucose.

In some embodiments, the composition further comprises a drug. In some embodiments, the drug is chemically attached to the particle. In some embodiments, the drug is physically absorbed onto the particle.

As used herein, the term "drug" refers to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. In some embodiments, the drug is anti-cancer therapeutic agent/chemotherapeutic agent. It is intended that the terms "anti-cancer therapeutic agent" and "chemotherapeutic agent" encompass anti-hyperproliferative and antineoplastic compounds as well as other biologically therapeutic compounds.

Pharmaceutical Composition

In some embodiments, the composition is in a pharmaceutically acceptable formulation.

As used herein, a "pharmaceutically acceptable formulation" may include any of a number of carriers such as solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Pharmaceutical compositions containing the presently described nanoparticles as the active ingredient can be prepared according to conventional pharmaceutical compounding techniques. See, for example, Remington's Pharmaceutical Sciences, 18th Ed., Mack Publishing Co., Easton, Pa. (1990). See also, Remington: The Science and Practice of Pharmacy, 21st Ed., Lippincott Williams & Wilkins, Philadelphia, Pa. (2005).

A composition may comprise different types of carriers depending on whether it is to be administered in solid, liquid or aerosol form, and whether it need be sterile for such routes of administration as injection.

Also contemplated are methods using compositions that are sterile solutions for injection or for application by any other route. A person of ordinary skill in the art would be familiar with techniques for generating sterile solutions for injection or application by any other route. Sterile injectable solutions are prepared by incorporating the active compounds in the required amount in an appropriate solvent with various other ingredients familiar to a person of skill in the art.

Suitable formulations can include, but are not limited to, injectable formulations including for example, solutions, emulsions, and suspensions. The compositions contemplated herein may take the form of solutions, suspensions, emulsions, combinations thereof, or any other pharmaceutical acceptable formulation as would commonly be known in the art.

In some embodiments, the carrier is a solvent. For a non-limiting example, the composition may be disposed in the solvent. Such a solvent includes any suitable solvent known in the art such as water, saline, phosphate-buffered saline.

The formulation of the composition may vary depending upon the route of administration. For parenteral administration in an aqueous solution, for example, the solution should be suitably buffered if necessary and the liquid diluent first rendered isotonic with sufficient saline or glucose. Sterile aqueous media which can be employed will be known to those of skill in the art in light of the present disclosure.

Supplementary active ingredients can also be incorporated into the compositions. For human administration, preparations should meet sterility and general safety and purity standards as required by FDA Office of Biologics standards. Administration may be by any known route.

In certain embodiments, a pharmaceutical composition includes at least about 10, 20, 30, 40, 50, 60, 70, 80, 90, 100, 200, 300, 400, 500, or more mg/mL of the gold nanoparticles disclosed herein.

The pharmaceutical composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. The composition must be stable under the conditions of manufacture and storage, and preserved against the contaminating action of microorganisms, such as bacteria and fungi. It will be appreciated that exotoxin contamination should be kept minimally at a safe level, for example, less than 0.5 ng/mg protein.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. In many cases, it will be preferable to include isotonic agents, such as, for example, sugars, sodium chloride or combinations thereof.

In other embodiments, a nasal solutions or sprays, aerosols or inhalants may be used. Nasal solutions are usually aqueous solutions designed to be administered to the nasal passages in drops or sprays.

Solid compositions for oral administration are also contemplated. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, edible carriers or combinations thereof. In other aspects, the oral composition may be prepared as a syrup or elixir. Additional formulations which are suitable for other modes of administration include suppositories. Suppositories are solid dosage forms of various weights and shapes for insertion into the rectum, vagina or urethra.

Sterile injectable solutions are prepared by incorporating the active compounds (e.g., nanoparticles) in the required amount in the appropriate solvent with various other ingredients enumerated above. The liquid medium should be suitably buffered if necessary and the liquid diluent first rendered isotonic prior to injection with sufficient saline or glucose.

Upon formulation, solutions will be administered in a manner compatible with the dosage formulation and in such amount as is effective. For example, the gold nanoparticles of the instant invention may be administered in such an amount as is effective for a particular imaging application desired.

The composition can be administered to the subject using any method known to those of ordinary skill in the art. The mode of administration may vary based on the application. For example, the mode of administration may vary depending on the particular cell, tissue, organ, portion of the body, or subject to be imaged. For example, the composition may be administered intravenously, intracerebrally, intracranially, intrathecally, into the substantia nigra or the region of the substantia nigra, intradermally, intraarterially, intraperitoneally, intralesionally, intratracheally, intranasally, topically, intramuscularly, intraperitone ally, subcutaneously, orally, topically, locally, inhalation (e.g., aerosol inhalation), injection, infusion, continuous infusion, localized perfusion bathing target cells directly, via a catheter, via a lavage, in crèmes, in lipid compositions (e.g., liposomes), or by other method or any combination of the forgoing as would be known to one of ordinary skill in the art (Remington's, 1990).

In particular embodiments, the composition is administered to a subject using a drug delivery device. Any drug delivery device is contemplated for use in delivering the gold nanoparticles of the instant invention to a subject.

An effective amount of the gold nanoparticle composition is determined based on the intended goal, for example, based on the imaging method and the subject or portion of a subject to be imaged. The quantity to be administered may also vary based on the particular route of administration to be used. The composition is preferably administered in a "safe and effective amount." As used herein, the term "safe and effective amount" refers to the quantity of a composition which is sufficient for the intended goal (e.g., imaging) without undue adverse side effects (such as toxicity, irritation, or allergic response).

A pharmaceutical composition to be administered to a subject may include at least about 10, 20, 30, 40, 50, 60, 70, 80, 90, 100, 200, 300, 400, 500, or more mg/mL of the gold nanoparticles disclosed herein. In some embodiments, the composition is administered at a concentration of about 20-40 milligrams/milliliter of the gold nanoparticles. In some embodiments, the composition is administered at a concentration of about 30-70 milligrams/milliliter of the gold nanoparticles. In other embodiments, the composition is administered at a concentration of about 40-70 milligrams/milliliter. In some aspects, the composition may be administered at a dosage of at least 0.1, 0.2, 0.3, 0.4, 0.5, 0.6, 0.7, 0.8, 0.9, 1.0, 2.0, 3.0 or more mL of a 30-80 mg/mL solution per 500 grams weight of a subject. In some embodiments wherein the subject is a small animal, such as a mouse or a rat, a dosage of 5-20 milligrams of the nanoparticles may be administered, depending on the size of the subject. In some embodiments wherein the subject is a large animal, such as a human, a dosage of 10-30 gram of the gold nanoparticles may be administered, depending on the size of the subject.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art.

Producing the Composition

Gold nanoparticles (AuNP) may be synthesized using a citrate acid reduction method, such as reported in (Hayat, 1990; Hayat, 1991; Slot and Geuze, 1985), each of which is hereby incorporated by reference. Solvents useful in creating AuNPs include, but are not limited to deionized water, a saline-containing solution, or phosphate buffered saline (PBS).

Methods of attaching PEG to a gold nanoparticle are known in the art. For a non-limiting example, where a PEG comprising a mercapto group (SH) is used, PEG is attached to the gold nanoparticle by thiol binding.

For a non-limiting example, the composition of the invention may be produced by stirring PEG consisting of mercapto group (SH) and a carboxyl group (COOH) with the gold nanoparticles to absorb the PEG onto the gold nanoparticles via the mercapto group. Next, for covalently attaching 2-deoxy-D-glucose to the carboxyl group of PEG, NHS ((N-Hydroxysulfosuccinimide sodium salt) and EDC (1-Ethyl-3-(3-dimethylaminopropyl) carbodiimide HCl) may be added to form an active ester intermediate with the carboxyl group, which can then undergo an amidation reaction with the NH2 group of 2-Amino-2-deoxy-D-glucose.

Diagnostic and Therapeutic Use of the Composition

According to another embodiment, the invention provides a method of imaging a tumor. The method comprises the steps of: administering to a subject the composition of the invention, wherein the composition penetrates to and accumulates in tumor cells of the subject; and scanning the subject or a portion thereof, thereby imaging the tumor cells. In some embodiments, the composition is utilized for imaging tumors overexpressing GLUT-1.

In some embodiments, a portion of a subject include any area of interest of a subject's body.

In some embodiments, administering is by oral administration. In some embodiments, administering is by injection. In some embodiments, administering is by an intravenous injection.

In some embodiments, scanning the subject is performed by an imaging technique that utilizes penetrating radiation. In some embodiments, scanning the subject is performed by a diagnostic imaging technique such as x-ray imaging, computed tomography (CT), ultrasound (US), magnetic resonance imaging (MRI). In some embodiments, scanning the subject is performed by a computed X-ray tomography (CT) scanning.

In some embodiments, the scanning step is performed 0.5 to 24 hours post the administering step. In some embodiments, the scanning step is performed 0.5 to 12 hours post the administering step. In some embodiments, the scanning step is performed 1 to 12 hours post the administering step. In some embodiments, the scanning step is performed 1 to 6 hours post the administering step. In some embodiments, the scanning step is performed within 24 hours from the administering step. In some embodiments, the scanning step is performed within 12 hours from the administering step. In some embodiments, the scanning step is performed within 6 hours from the administering step.

As used herein, the term "subject" refers to any animal (e.g., a mammal), including, but not limited to, humans, non-human primates, rodents, and the like (e.g., which is to be the recipient of a particular treatment, or from whom cancer stem cells are harvested). Typically, the terms "subject" and "patient" are used interchangeably, unless indicated otherwise herein.

In some embodiments, the subject is a human subject. In some embodiments, the subject is a human subject at risk of being afflicted with cancer. In some embodiments, the subject is diagnosed with a cancer. In some embodiments, the cancer is a cancer associated with GLUT-1 overexpression.

As used herein, the term "subject at risk of being afflicted with cancer" refers to a subject that presents one or more signs or symptoms indicative of a cancer (e.g., a noticeable lump or mass) or is being screened for a cancer (e.g., during a routine physical). A subject at risk of being afflicted with cancer may also have one or more risk factors. A subject at risk of being afflicted with cancer encompasses an individual that has not been previously tested for cancer. However, a "subject at risk of being afflicted with cancer" also encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission).

A "subject at risk of being afflicted with cancer" may be diagnosed with cancer or alternatively found not to have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests.

In some embodiments, the subject is a human subject afflicted with cancer. In some embodiments, the subject is afflicted with cancer and the imaging method is used for determining the stage of the cancer. In some embodiments, the subject afflicted with cancer was treated with anti-cancer drug, and the imaging method is used for follow up of the treatment.

In some embodiments, the method further comprises the step of analyzing the imaging data. In some embodiments, treatment decision may be not to administer a therapy when a tumor was not imaged. In some embodiments, the analysis of the imaging data is used for deciding on a route of treatment adequate to the patient. In some embodiments, deciding on a route of treatment adequate to the patient depends on tumor size and location, on the stage of the disease, as well as on the health state of the patient. In some embodiments, the route of treatment include one or more protocols of treatment selected from the group consisting of: surgery, radiosurgery, chemotherapy, a treatment comprising administration of cytostatic(s), cytotoxic(s), a targeted therapy, a vaccine, radionuclides, immune-radionuclides, and any other biological or inorganic product intended to treat cancer. In some embodiments, a treatment is administered subsequent to the imaging. In some embodiments, a treatment is administered to the subject in real time, while imaging the tumor. For a non-limiting example a radiation treatment may be administered to the location of the tumor while imaging the tumor. In another non-limiting example, imaging the tumor may be helpful prior and post a surgery to remove the tumor.

In some embodiments, where the composition further comprises a drug, the composition serves both for diagnostic imaging and as a therapeutic agent. In some embodiments, imaging and treating the tumor is performed simultaneously. In some embodiments, the drug may be activated in the tumor subsequent to imaging such as by using ultrasound (US) waves to release the drug from the composition. In some embodiments, the drug remains attached to the nanoparticle of the composition and is used to treat tumor cells.

In some embodiments, the nanoparticles of the composition are radiation absorbing nanoparticles. As used herein, the term "radiation absorbing nanoparticles" refers to nanoparticles which absorb electromagnetic radiation (including as non-limiting examples infrared, near-infrared (NIR) and radio-frequency (RF) radiation) and convert the absorbed energy to released heat which can be used to create localized hyperthermia. In some embodiments, the composition is used for thermal ablation of tumor cells in which the composition accumulates, without causing damage to surrounding normal tissues or substantial toxicity to the subject. As used herein ablation refers to the destruction of cells. Methods for irradiating a tissue comprising metal nanoparticles for enhancing effects of radiation therapy, are known in the art. For example, U.S. 2005/0020869 discloses the use of gold nanoparticles for administration to enhance the effects of radiation therapy.

According to some embodiments, the invention provides a method for diagnosing and/or treating cancer. The method comprises the steps of: administering to a subject the composition of the invention, wherein the composition reach to and accumulates on/in tumor or metastases of the subject; scanning the subject or a portion thereof, thereby imaging the tumor, and directing ionizing irradiation (e.g., x-ray) to the composition to obtain locally enhanced radiation therapy within the tumor. A person with skill in the art will appreciate that the gold nanoparticles (GNPs) are used as radiosensitizing agents. Typically, materials having high atomic number, such as gold (Z=79) increase radiation sensitivity due to their high absorption of photons and release of secondary energy in the form of photoelectrons, auger electrons, and x-rays into surrounding tissue.

In some embodiments, the invention provides a method for treating or suppressing cancer. In some embodiments, the method comprises the steps of: administering to a subject the composition of the invention, wherein the composition reach to and accumulates on/in tumor or metastases of the subject; and directing ionizing irradiation (e.g., x-ray) to the composition to obtain locally enhanced radiation therapy within the tumor or metastases.

In some embodiments, the composition further comprises anti-cancer therapeutic agent/chemotherapeutic agent. In some embodiments, the anti-cancer therapeutic agent/chemotherapeutic agent exhibits local toxicity to cells within the tumor or metastases. In such embodiments, the anti-cancer therapeutic agent/chemotherapeutic agent may mediate a locally enhanced cell death (e.g., by apoptosis) or cell growth arrest, within cells of the tumor or metastases.

In some embodiments, the method comprises the step of administering to a subject the composition of the invention further comprising anti-cancer therapeutic agent/chemotherapeutic agent, wherein the composition reach to and accumulates in tumor or metastases of the subject, thereby obtaining locally enhanced cell death (e.g., by apoptosis) or cell growth arrest within cells of the tumor or metastases. In some embodiments, the method further comprises the step of directing ionizing irradiation (e.g., x-ray) to the composition to obtain locally enhanced radiation therapy within the cells of the tumor or metastases.

As used herein, the terms "treatment" or "treating" of a disease, disorder, or condition (e.g., cancer associated with GLUT-1 overexpression) encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

The term "suppression" is used to describe a condition wherein the disease/disorder process has already begun but obvious symptoms of the condition have yet to be realized. Thus, the cells of an individual may have the disease/disorder but no outside signs of the disease/disorder have yet been clinically recognized. In either case, the term prophylaxis can be applied to encompass both prevention and suppression. Conversely, the term "treatment" refers to the clinical application of active agents to combat an already existing condition whose clinical presentation has already been realized in a patient.

In some embodiments, the invention provides kits comprising one or more compositions disclosed herein. In some embodiments, the invention provides kits useful for methods disclosed herein. For example, a kit may include a container having a sterile reservoir that houses any composition disclosed herein. In some embodiments, the kit further includes instructions. For example, a kit may include the instructions for administering the composition to a subject (e.g., indication, dosage, methods etc.). In yet another example the kit may include instructions of to apply the compositions and methods of the invention to imaging systems e.g., computed tomography (CT), ultrasound (US), magnetic resonance imaging (MRI)

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as polymer subunits, size or thickness, are to be understood to include any integer within the recited range, unless otherwise indicated.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise," "include" and "have" and conjugates thereof, are used to indicate that the object or objects of the verb are not necessarily a complete listing of components, elements or parts of the subject or subjects of the verb. Other terms as used herein are meant to be defined by their well-known meanings in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additional objects, advantages, and novel features of the present invention will become apparent to one ordinarily skilled in the art upon examination of the following examples, which are not intended to be limiting. Additionally, each of the various embodiments and aspects of the present invention as delineated herein above and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Materials and Methods:

Gold Nanoparticle Synthesis, Conjugation and Characterization

Synthesis:

Synthesis of 20 nm spherical GNPs was carried out using sodium citrate as a reducing agent, based on Enüstûn & Turkevic's methodology. 4144, of 50% w/V HAuC14 solution were added to 200 mL purified water, and the solution was heated in an oil bath on a heating plate until boiling. Then, 4.04 mL of sodium citrate tribasic dihydrate (Sigma-Aldrich) 10% solution were added, and the solution was stirred for 10 min. After cooling to room temperature, the solution was centrifuged until separation between nanoparticles and a redundant clear solution.

Conjugation:

120 µL of 50 mg/mL PEG7 solution (O-(2-Carboxyethyl)-O'-(2-mercaptoethyl) heptaethylene glycol) (Sigma-Aldrich) were added to the nanoparticles solution, and the solution was stirred for 4 h at room temperature. Following this step, 200 µL of 10 mg/mL EDC solution (1-Ethyl-3-(3-dimethylaminopropyl) carbodiimideHCl) (Thermo Scientific) and 200 µL of 10 mg/mL NHS solution (N-Hydroxysulfosuccinimide sodium salt) (Sigma-Aldrich) were added to the nanoparticles solution. The following four glucosamine molecules were used for glucosamine conjugation: b-D-Glucopyranosyl amine (Carbosynth), 2-Amino-2-deoxy-D-glucose HCl (Sigma-Aldrich), 3-Amino-3-deoxy-D-glucose HCl (Carbosynth) and 6-Amino-6-deoxy-D-glucose HCl (Appolo Scientific). Each of these glucosamine molecules were added in excess, one at the time, resulted in four types of GF-GNPs (denoted as 1GF-GNP, 2GF-GNP, 3GF-GNP and 6GF-GNP). Centrifugation was performed until a final Au concentration of 30 mg/mL was reached.

Characterization:

Transmission electron microscopy (TEM, JEM-1400, JEOL) was used to measure size and shape of the GNPs, which were further characterized using ultraviolet-visible spectroscopy (UV-Vis; UV-1650 PC; Shimadzu Corporation, Kyoto Japan) and Zeta potential (ZetaSizer 3000HS; Malvern Instruments, Malvern, UK), following each level of coating.

In-Vitro Cell Binding Study

Human SCC A431 cells ($1 \times 10^6$) were cultured in 5 ml glucose-free DMEM medium containing 5% FCS, 0.5% Penicillin and 0.5% Glutamine. Then, excess amounts of GNPs (four types, mentioned above) were added and incubated with cells for 30 minutes at 37° C. Each experimental group was run in triplicate. For temperature dependence experiment, Incubation of the cells with 2GF-GNPs was carried out at both 37° C. and 4° C., for 30 minutes. At the case of incubation at 4° C., the cells were also pre-incubated at 4° C. for 30 minutes before treatment with the GNPs. For competitive experiment with high glucose level, A431 cultures were saturated with free glucose (10 mg/mL final concentration in comparison to original concentration of 4.5 mg/mL) for 30 minutes before adding the GNPs, and throughout the incubation with the GNPs. Incubation with the GNPs in this assay was for 20 min, 30 min and 120 min. For cytochalasin B inhibition test, cytochalasin B (Cayman Chemical) was added to the medium (100 μs/ml final concentration) for two hours incubation. Then, the medium was removed and the cells were washed three times with PBS before adding GNPs. Inhibition was examined after 20 min, 30 min and 120 min incubation with the GNPs. In all these experiments, after incubation with the GNPs the medium was washed twice with PBS, followed by trypsin treatment. The cells were centrifuged twice (7 minutes in 1000 rpm) in order to get rid of the unbound nanoparticles. Finally, aqua-regia was added to the cells for atomic absorption spectroscopy gold detection. Trypan blue viability test for the cells which were incubated with CB, was performed by staining the cells with 0.4% trypan blue at a dilution of 1:9 and counting using a hemocytometer.

Confocal Microscopy Experiment

1GF-GNPs, 2GF-GNPs, 3GF-GNPs, GF-GNPs were fluorescent coated (Rhodamine B, Sigma, Israel). Fluorescent coated (Rhodamine B, Sigma, Israel) GF-GNPs ("Rhodamine B-GF-GNP complex") were incubated with A431 cells for 30 min at 37° C. The cells were subsequently washed three times in PBS prior to confocal imaging using Leica TCS SP5 with Acousto-Optical Beam Splitter microscope to acquire fluorescent and bright field images.

Sample Preparation for TEM

Sample preparation for TEM: 4 Petri dishes were seeded with 500,000 A431 Human SCC cancer cells for each dish. 5 ml DMEM medium (without glucose) was added to each one of the dishes. Cells were incubated at 37° C. for 48 hours without medium replacement. DMEM medium was removed. Cells were fixed with 2 ml glutaraldehyde per dish. The cells were incubated for 1 h in room temperature followed by scraping of the cells with a rubber policeman into Eppendorf tubes. Cells were then washed with Cacodylate buffer, 1% Osmium, 70%, 90%, 100% Alcohol washing twice, 1:0, 3:1, 1:3 Propilen oxide:AGAR washing.

Fluorescence-Activated Cell Sorter (FACS) Analysis of Nanoparticle Cellular Uptake Cells were incubated with 2GF-GNPs for 15 min at 37° C. and 4° C. and then washed with PBS, followed by trypsin treatment. Then, cells were centrifuged twice (5 min in 1000 rpm) to wash out unbound nanoparticles. At the case of incubation at 4° C., cells were kept on ice for 10 min prior to experiment to inhibit endocytosis and all the solutions were pre-cooled on ice to maintain experimental conditions strictly at 4° C. Cells were harvested using trypsin and analyzed for cell-associated NPs by FACS (Cellquest software; Becton-Dickinson & Co., Franklin Lakes, N.J.).

Animal Model and In Vivo Experiments

In Vivo Tumor Uptake of GF-GNP:

A431 cells ($2\times10^6$) were injected subcutaneously into the back flank area of nude mice aged 6 weeks. When the tumor reached a diameter of 4-5 mm, the four types of GF-GNPs (200 μL, 30 mg/mL) were intravenously injected into their tail vein (5 mice per group). Experimental procedure was identical for all four GF-GNP types. 3.5 h post IV injection the animals were scanned by micro-CT scanner and then sacrificed. Gold concentration in the tumor and major organs (kidney, liver, spleen and plasma (data not shown)) was quantitatively measured by atomic absorption spectroscopy.

Differentiation Between Tumor and Inflammation:

Human SCC xenografts and inflammation were established in 14 mice. First, mice were inoculated subcutaneously in the left hind leg with $2\times10^6$ SCC-A431 cells. Once the tumor reached the appropriate size of 4-5 mm, inflammation was established in the back, behind lung, by a subcutaneous injection of 100 (micro liters) μL of turpentine oil 19. Four days post turpentine injection, [$^{18}$F]FDG was IV injected into four mice. [18F]FDG-PET/CT scans were performed to these mice at 40 to 60 min post injection. In addition, 2GF-GNPs were IV injected to all mice. CT scans were performed before injection and 3.5 hours post injection. Then, mice were sacrificed and gold concentration was quantitatively measured in the tumor and inflammation by atomic absorption spectroscopy.

CT Analysis

CT scans were performed using a micro-CT scanner (Skyscan High Resolution Model 1176) with nominal resolution of 35 μm, 0.2 mm aluminum filter, and tube voltage of 45 kV. Reconstruction was done with a modified Feldkamp algorithm using the SkyScanNRecon software accelerated by GPU. Ring artifact reduction, gaussian smoothing (3%), and beam hardening correction (20%) were applied. Volume rendered three-dimensional (3D) images were generated using an RGBA transfer function in SkyScan CT-Volume ("CTVol") software and in SkyScan CT-Voxel ("CT-Vox") software.

Atomic Absorption Spectroscopy Analysis

Atomic absorption spectroscopy (AA 140; Agilent Technologies, Santa Clara, Calif.) was used to determine amounts of gold in the investigated samples. Cell samples from the in-vitro experiments were dissolved in 100 μL aqua regia acid (a mixture of nitric acid and hydrochloric acid in a volume ratio of 1:3) and diluted with purified water to a total volume of 4 mL. Tissues taken in the in-vivo experiment were melted with 1 mL aqua-regia acid and then evaporated and diluted to a total volume of 4 mL. After filtration of the samples, gold concentrations were determined according to absorbance values, with correlation to calibration curves, constructed from solution with known gold concentrations.

Example 1

GF-GNPs Uptake by Tumor Cells

GF-GNPs were synthesized as described in the materials and methods section, and their interaction with cancer cells was studied, investigating whether the glucose molecule (~1 nm) retains some of its activity and can be recognized as glucose by cells, when conjugated to a 'large' GNP (20 nm). To this end, four types of GF-GNP were studied, wherein the GNP was attached selectively to one of four possible intramolecular glucosamine sites. The hydroxyl groups (—OH) of glucose can be substituted by amine groups (—NH2) in different and specific molecular sites, denoted 1, 2, 3 or 6 (C-1, C-2, C-3 and C-6, respectively). Identical, 20 nm GNPs were linked selectively to each of the 4 glucosamine sites, one at the time, resulting in four distinct GF-GNPs of the same shape and size, differing only in the intra-molecular glucose site being functionalized (FIG. 1). Characterization of the particles was performed using TEM, UV-Vis spectroscopy and Zeta potential.

Figure 2A:
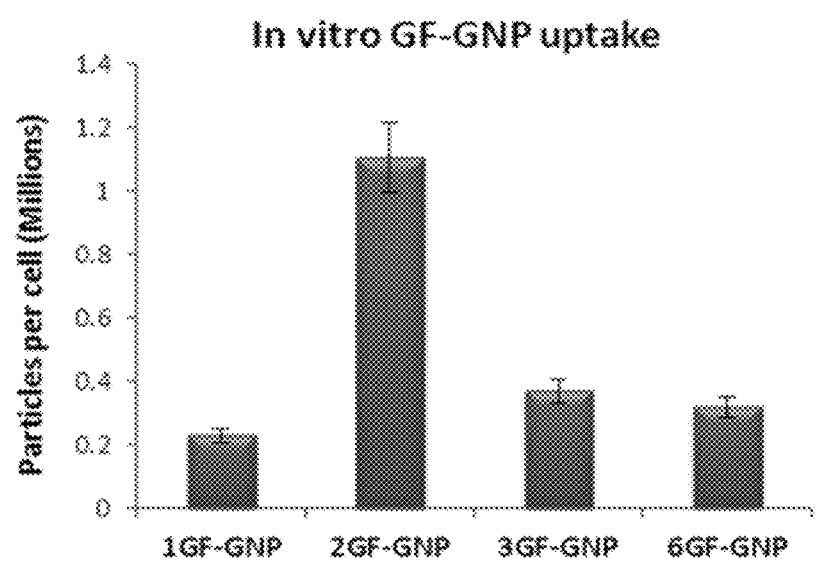
FIG. 2A is a bar graph presenting cellular uptake of the GF-GNPs of FIG. 1A into A431 SCC cell line, as measured by atomic absorption spectroscopy. Results presented as mean±SEM.

In order to examine the interaction between the GF-GNPs and cancer cells, first, an in vitro study was performed. The four types of GF-GNP were incubated with squamous cell carcinoma (SCC) human epidermoid A431 cancer cells (n=3 per group) for 30 minutes and atomic absorption spectroscopy was used to quantitatively determine the amount of internalized Au. Unexpectedly, despite their identical shapes and sizes, a significantly higher uptake was observed for the GNPs that were conjugated to glucose through its 2' carbon position (denoted as 2GF-GNP) (FIG. 2A). The uptake was about 3 times greater than that of the other three GNP types.

Figure 2B:
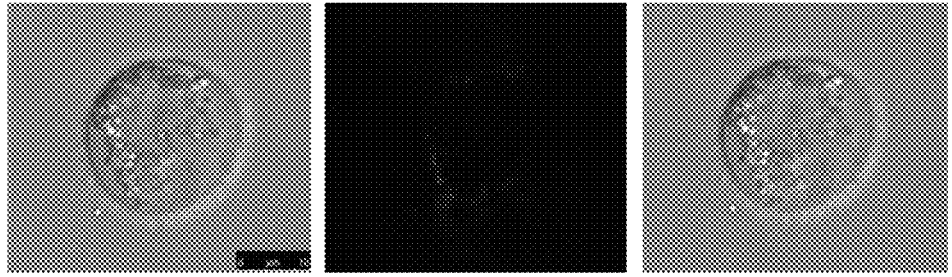
FIGS. 2B-E are confocal images of A431 cells following 30 min incubation with Rhodamine B-1GF-GNP complex (B); Rhodamine B-2GF-GNP complex (C); Rhodamine B-3GF-GNP complex (D); and Rhodamine B-6GF-GNP complex (E), images on the left column are bright field images of the cells, images on the middle column present fluorescent-coated 2GF-GNPs (red), and images on the right column are combined images.
Figure 2C:
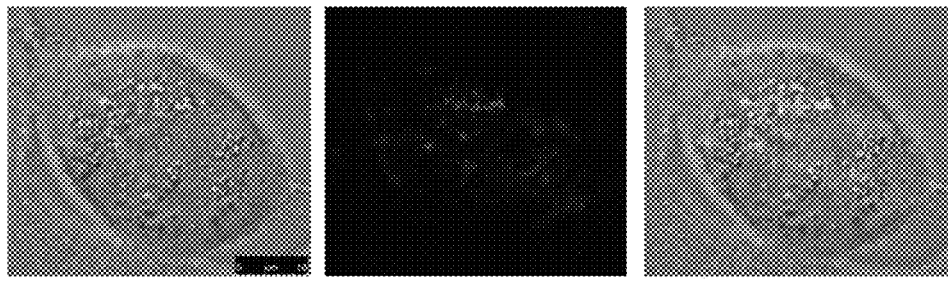
Figure 2D:
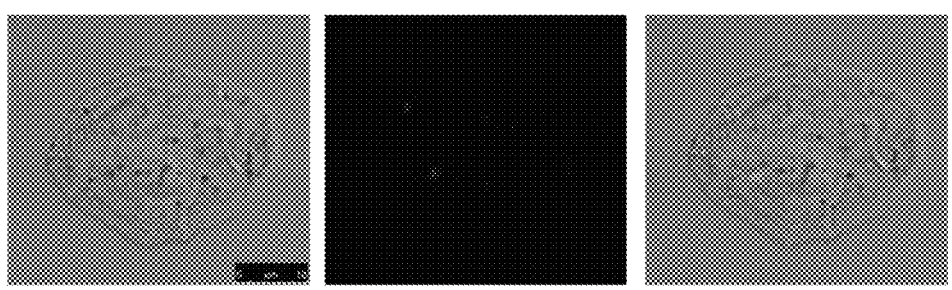
Figure 2E:
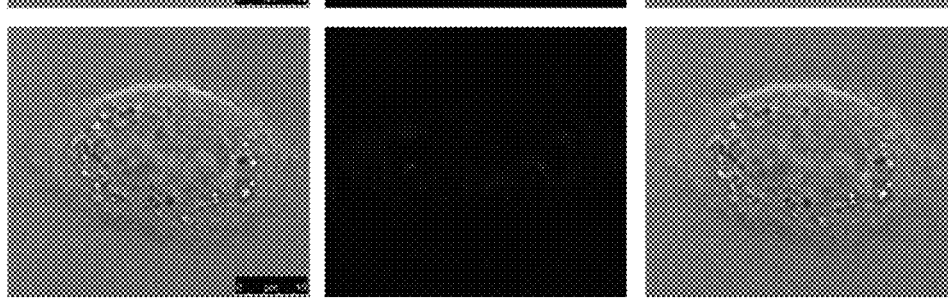

Further, internalization of the four types of fluorescent coated GF-GNPs into A431 cells was examined by confocal microscopy. To this end, A431 cancer cells were incubated with either Rhodamine B-1GF-GNP complex, Rhodamine B-2GF-GNP complex, Rhodamine B-3GF-GNP complex, and Rhodamine B-6GF-GNP complex. Confocal microscopy images of A431 cells showed higher cellular internalization for Rhodamine B-2GF-GNP complex (FIG. 2C) compared to Rhodamine B-1GF-GNP complex (FIG. 2B), Rhodamine B-3GF-GNP complex (FIG. 2D), and Rhodamine B-6GF-GNP complex (FIG. 2E). This Result further support the with the quantitative results that showed significantly higher uptake for 2GF-GNPs in comparison to the other three isomer-conjugates (1GF-GNP, 3GF-GFP, and 6GF-GNP).

Figure 2F:
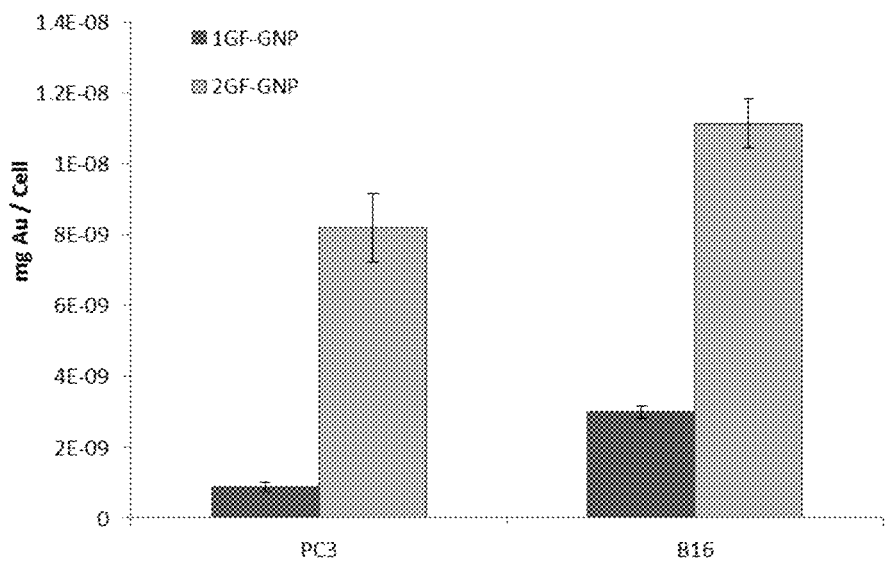
FIG. 2F is a bar graph showing cellular uptake of the 2GF-GNP and 1GF-GNP into PC3 or B16 cell lines.

In addition, the uptake of 2GF-GNP and the control 1GF-GNP was compared in additional cancer cells with high GLUT-1 expression (human prostate cancer cell line (PC3) and mouse melanoma cell line (B16)). Results demonstrated increased uptake of 2GF-GNP (FIG. 2F).

Figure 3A:
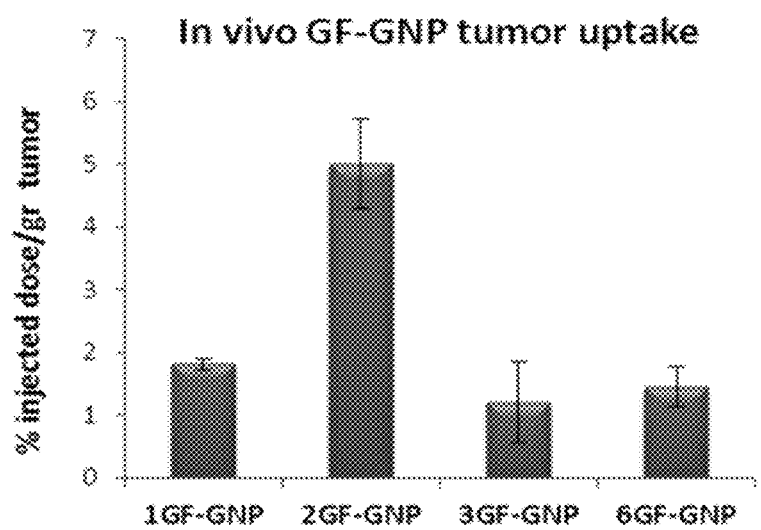
FIG. 3A is a bar graph presenting an in vivo tumor uptake of the GF-GNPs of FIG. 1A, as measured by atomic absorption spectroscopy. Results presented as mean±standard error mean (SEM)
Figure 3B:
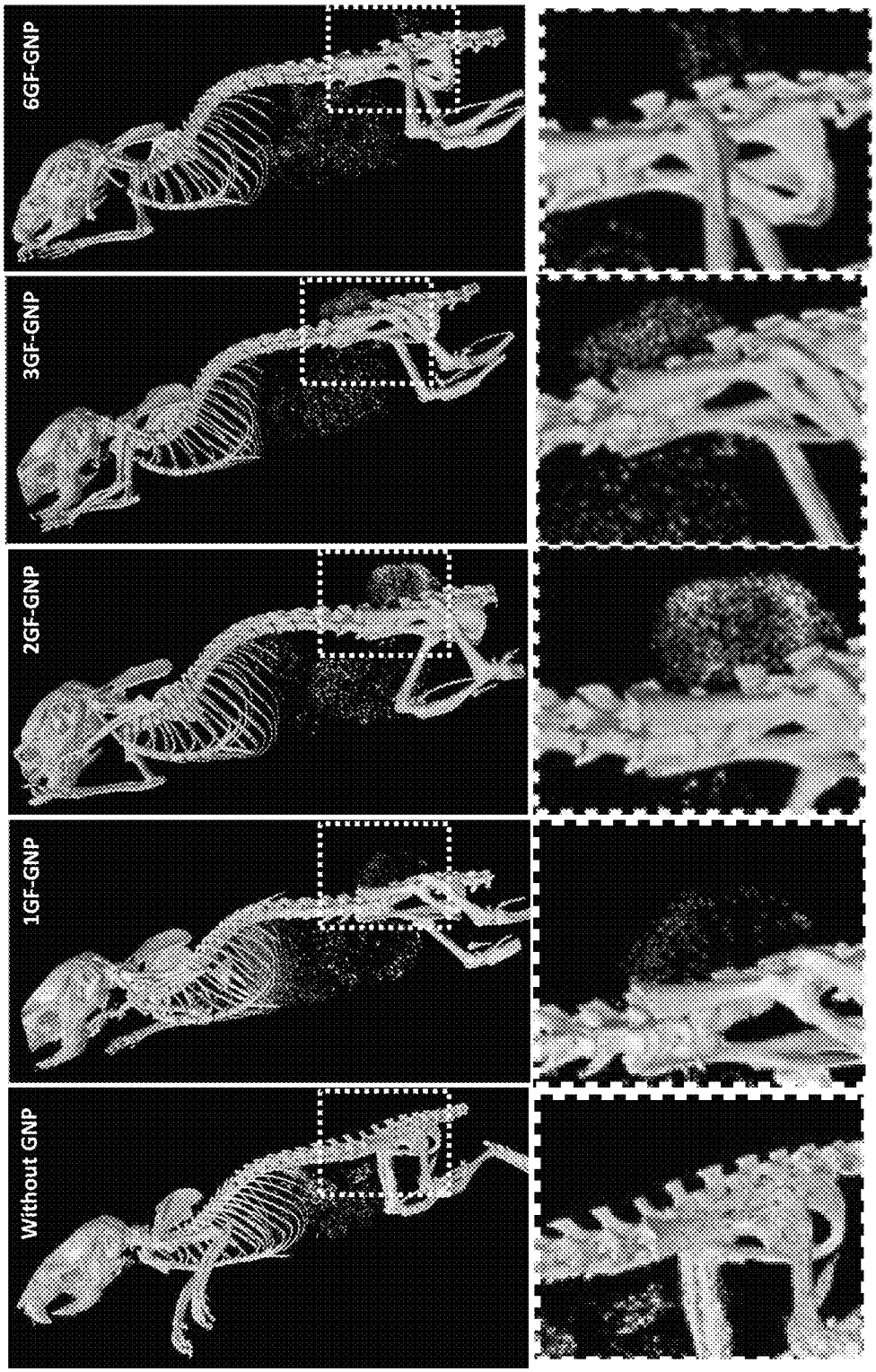
FIG. 3B shows CT volume-rendered images of five mice; one without nanoparticles (left), and four mice at 3.5 h post IV injection of the four types of GF-GNPs. Upper images: whole body volume-rendered images. The tumor area is marked with a white dashed rectangle. It is demonstrated that the tumor cannot be identified without injection of GNP (upper left image), while a significant accumulation of GNP can be observed following injection of 2GF-GNP. Some accumulation of GNP can be observed in the tumor area following injection of 1GF-GNP, 3GF-GNP and 6GF-GNP, which can be attributed to the passive targeting mechanism. For all mice, CT contrast is observed also in the digestive system due to food. In addition, in mice which were injected with GNPs, nanoparticles can be identified in the abdomen, as they accumulate in the kidneys, liver, and spleen according to their well-described clearance mechanism. Bottom images are enlarged images of the white marked tumor areas.

GF-GNPs uptake was further analyzed in vivo. GF-GNPs were intravenously (IV) injected into mice bearing human A431 tumors (n=5 for each group), and gold concentration in the tumor was quantitatively measured using atomic absorption spectroscopy. In addition, CT scans of the mice were performed pre-injection and at 3.5 h post-injection of the GF-GNPs. Both atomic absorption spectroscopy (FIG. 3A) and CT results (FIG. 3B) clearly demonstrated that the uptake of 2GF-GNP was significantly higher than that of the other three GF-GNP conjugates.

Unexpectedly though the four nanoparticle types (1GF-GNP, 2GF-GNP, 3GF-GNP, and 6GF-GNP) are of the same material (gold), coated by the same molecule (glucosamine) and have the same physicochemical characteristics, while differing only in the intra-molecular glucose conjugation site, both in vitro and in vivo experiments showed a remarkably selective accumulation of one of the four isomers (2GF-GNP, FIGS. 2A, 2B-E, FIG. 3A-B). This difference in uptake provides unequivocal evidence that the 2GF-GNPs are recognized and preferred by cancer cells, probably because of the specificity of the glucose coating. Interestingly, the 2' carbon position is also the one to which the $^{18}$F is connected in [$^{18}$F]FDG, supporting our result that chemical modification of the 2' carbon position does not prevent glucose recognition by cells. In addition, the differential uptake in vivo underscores the distinction between passive targeting of the 1GF-GNP, 3GF-GNP and 6GF-GNP, which is due to the enhanced permeability and retention (EPR) effect and metabolically active targeting of the 2GF-GNP. Most importantly, the results markedly show that small tumors (approximately 4-5 mm in diameter), which are undetectable by CT without the use of GNP contrast agents, become clearly visible and detectable following administration of 2GF-GNP, which like FDG can detect glucose metabolic activity while inducing distinct contrast in CT imaging.

Example 2

2GF-GNPs Uptake Differentiates Tumor Cells from Inflammatory Cells

Typically, newly formed blood vessels in growing tumors typically differ from those in different pathologic conditions, including inflammation, therefore the ability of the proposed nanoparticle-based technique may provide the ability to differentiate tumors from non-malignant metabolically active processes (inflammations and infections). Although both inflammatory and tumor tissues exhibit an EPR effect, tumor vasculatures have unique characteristics, as they are irregular in size, shape, and branching pattern. In addition, they do not have a normal vascular hierarchy and they exhibit defects in endothelial cell barrier function, which enhances vessel leakiness. Furthermore, while infection is characterized by increasing blood flow and development of an expanded network of lymphatics, most blood vessels in tumors exhibit marginal blood flow and highly impaired lymphatic drainage, enabling retention of macromolecules in the tumor. These dissimilarities have led to examine whether 2GF-GNPs accumulates and retain in the tumor to a greater extent than in the inflammation, allowing a differentiation between the two.

The abilities of 2GF-GNPs and of [$^{18}$F]FDG to differentiate A431 tumors from turpentine-induced inflammation in a combined tumor-inflammation mouse model, were compared. Inflammation was established in mice bearing A431 tumors (n=14) by a subcutaneous injection of turpentine oil, and four days post turpentine injection, 2GF-GNP or [$^{18}$F]FDG were IV injected. It has been previously demonstrated that maximum uptake of [$^{18}$F]FDG occurs 4 days post injection in this inflammation model, and therefore, this time point was selected for imaging. CT scans were performed 3.5 hours after 2GF-GNP injection, and after animal were sacrificed, gold concentration in the tumor and in the inflammatory lesion were quantitatively measured by atomic absorption spectroscopy.

Figures 4A, 4B, 4C:
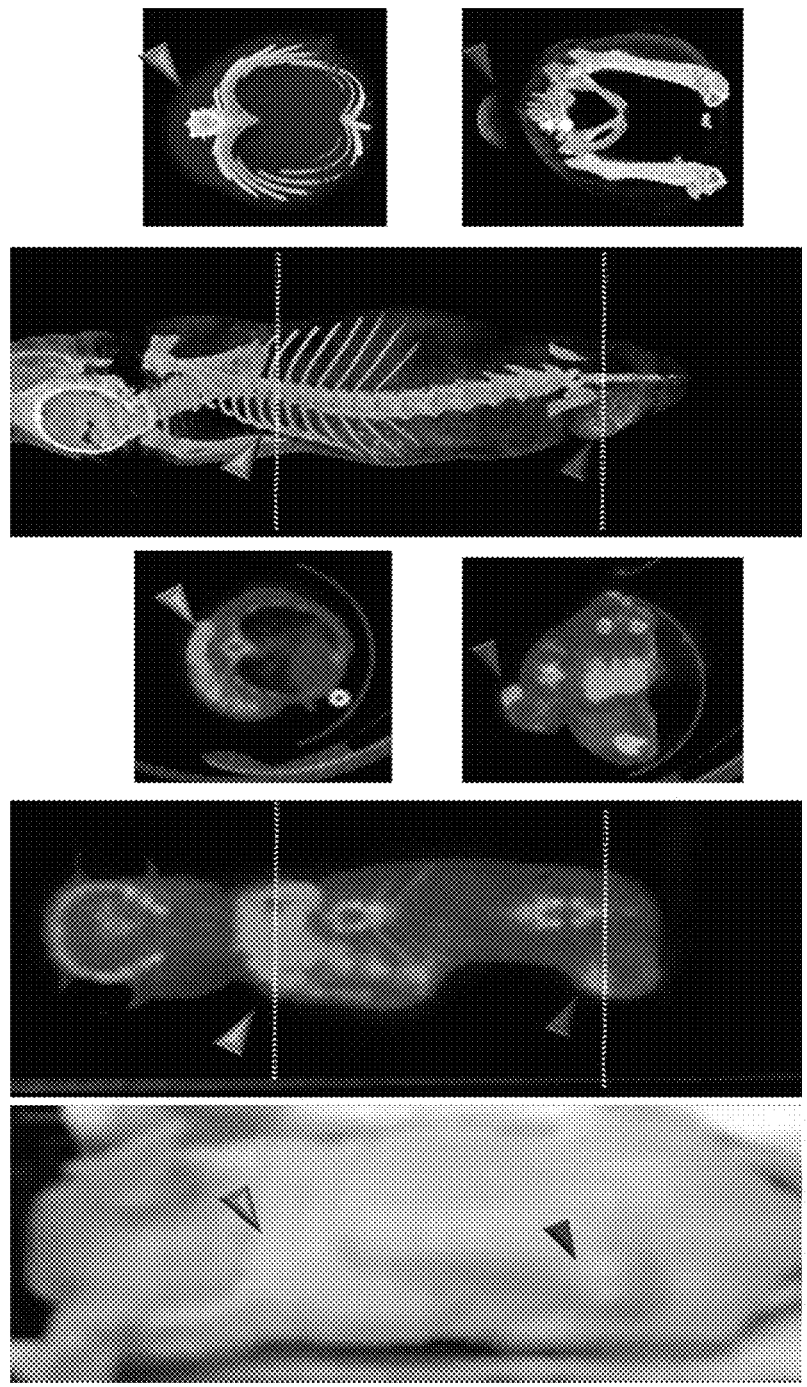
FIGS. 4A-D show differentiation between cancer and inflammation: green arrowheads indicate location of inflammation; red arrowheads indicate location of A431 tumors, (A) representative image of a combined tumor & inflammation mouse model, before 2GF-GNP injection, (B) [$^{18}$F] FDG-PET/CT slice images of a representative mouse at 40-60 min post injection. [$^{18}$F]FDG accumulates equally in both tumor and inflammation, and does not distinct between them, (C) CT surface-rendered images of the same mouse at 3.5 hours post intravenous (IV) injection of 2GF-GNP. Gold accumulation is observed in the tumor, yet not in the inflammation, allowing a clear distinction between the two, (D) a bar graph showing atomic absorption spectroscopy measurements of 2GF-GNP accumulation in tumor and inflammation. Results presented as mean±SEM.
Figure 4D:
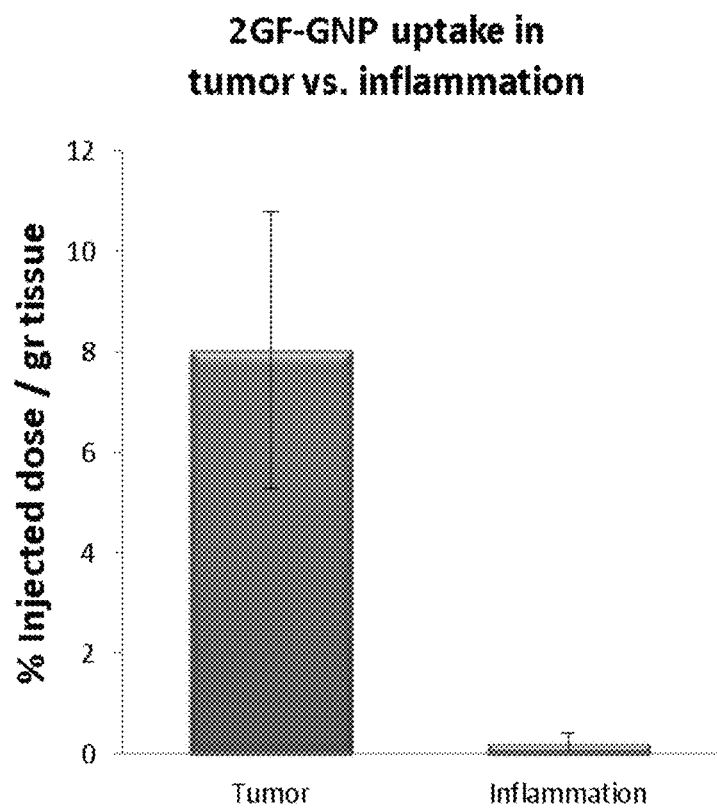

Interestingly, both CT (FIG. 4C) and atomic absorption spectroscopy (FIG. 4D) results showed high-density accumulation of gold in the tumor, while practically no gold was detected in the inflammation region. For comparison, [$^{18}$F]FDG PET-CT scans were performed on three mice at 40-60 minutes after [$^{18}$F]FDG injection, showing no differentiation between cancer and inflammation, which exhibited equal accumulation of the radioactive tracer (FIG. 4B).

Example 3

Internalization Mechanism of 2GF-GNPs by Tumor Cells

In order to study potential mechanism that triggers the uptake of 2GF-GNP by tumors, an in vitro study with A431 cells was performed. Since the uptake of both glucose and FDG is closely related to the GLUT-1 glucose transporter, and GLUT-1 has been found to be highly over-expressed in the majority of cancers which present high [$^{18}$F]FDG avidity, it was hypothesized that GLUT-1 plays a key role in the uptake mechanism of 2GF-GNP.

Without wishing to be bound by a specific mechanism it was hypothesized that the relatively large size of the 2GF-GNP (compared to that of glucose) prevents its uptake through glucose transporters, therefore GLUT-1 may trigger a cascade of events that eventually leads to the increased uptake of the 2GF-GNP complex by cancer cells, possibly through endocytosis.

Figure 5A:
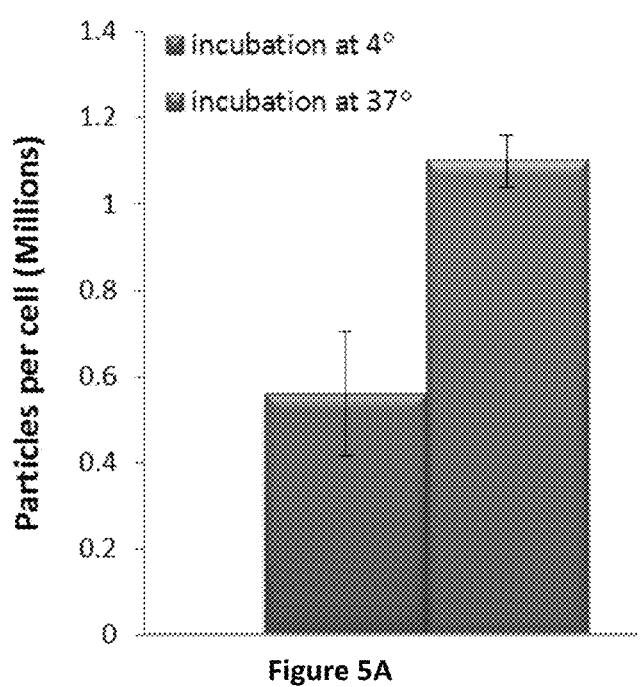
FIG. 5A is a bar graph presenting cellular uptake of the 2GF-GNPs into A431 cells, under 37° C. in comparison to 4° C. as measured by atomic absorption spectroscopy.
Figure 5B:
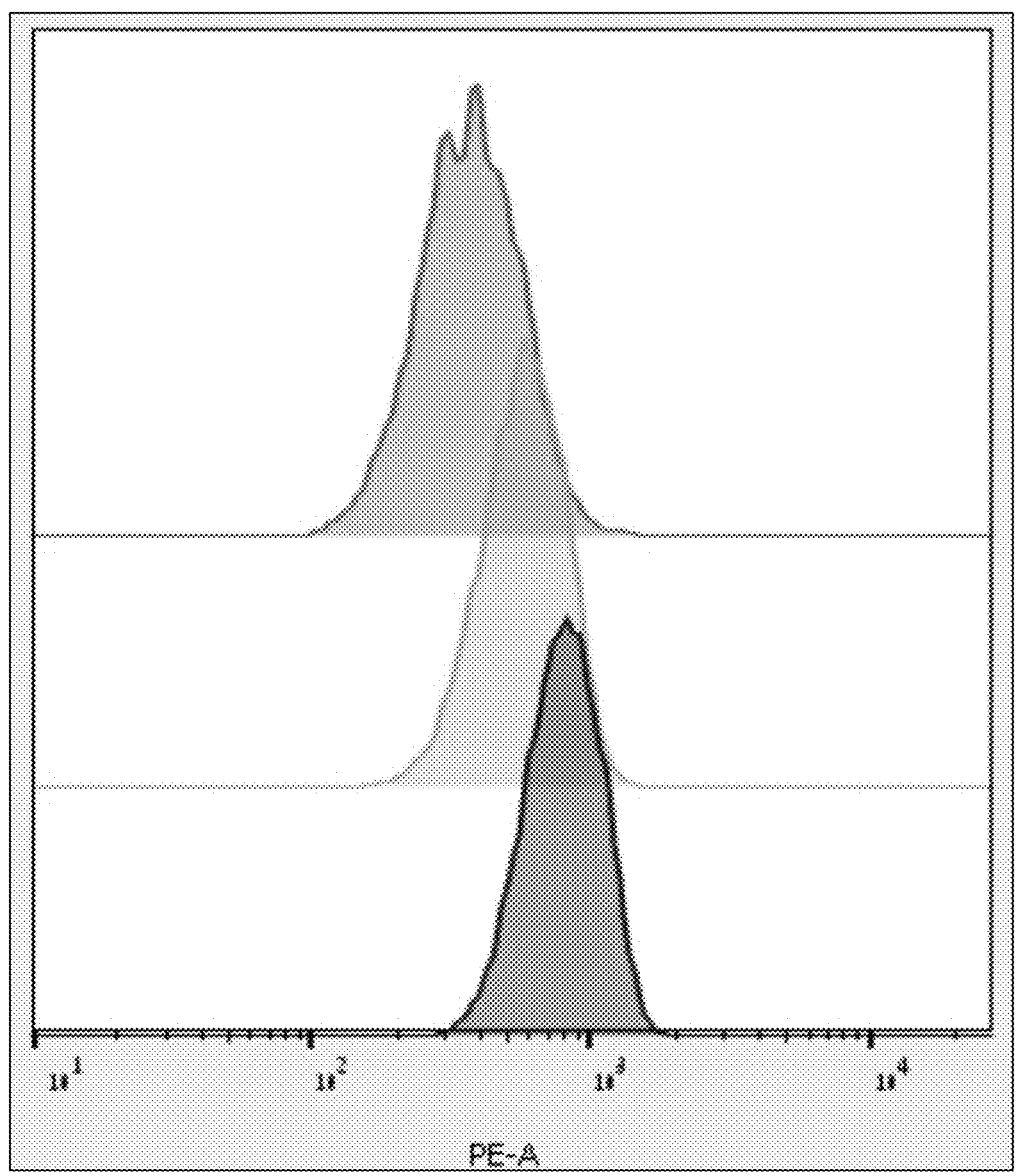
FIG. 5B shows representative histograms of GNP binding and uptake in cancer cells determined by flow cytometry (FACS), red: control cancer cells (without GNPs), orange: cancer cells loaded with GNPs in 4° C.; blue: cancer cells loaded with GNPs in 37° C.

Therefore, experiments were focused on investigating the effect of GLUT-1, as well as on validating the endocytic pathway. An initial step towards investigating the internalization mechanism of 2GF-GNP was done by incubating A431 cells with 2GF-GNP at 4° C. and 37° C., given that endocytosis is an energy-dependent process. As demonstrated by atomic absorption spectroscopy (FIG. 5A) and FACS analysis (FIG. 5B), 2GF-GNPs were internalized to a significantly lesser extent when kept at 4° C. compared to 37° C., suggesting that internalization into the cells occurs, at least partially, through an endocytic pathway.

Figure 5C:
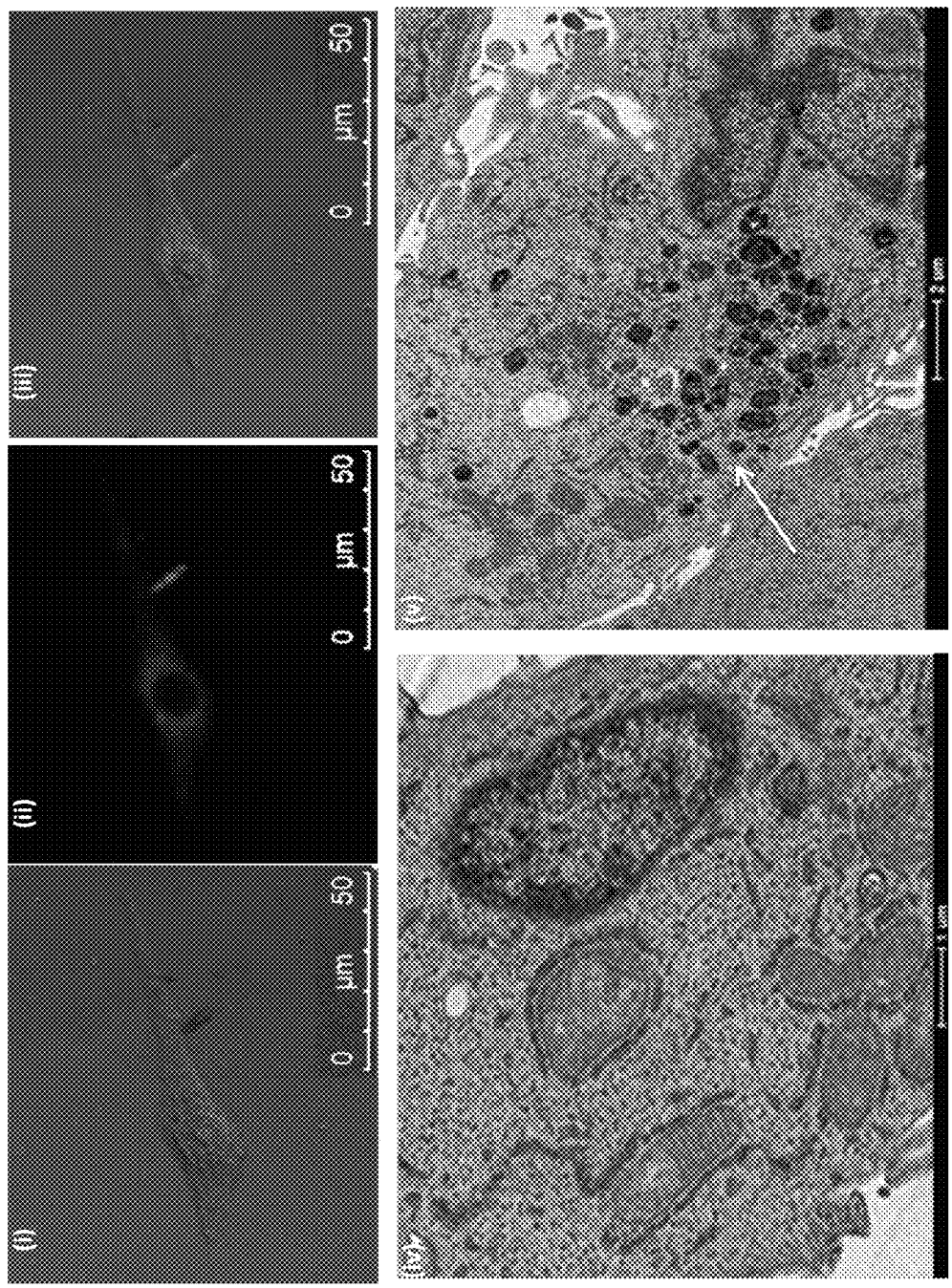
FIG. 5C (i)-(iii): are confocal images of A431 cells after 30 min incubation with Rhodamine B-2GF-GNP complex: (i) bright field image of the cell, (ii) fluorescent-coated 2GF-GNPs (purple), (iii) combined images, (iv)-(v): TEM images of A431 cancer cells: (iv) A431 cells without GNPs, (v) after 30 min incubation with 2GF-GNP. White arrow points at the accumulation of well-defined nanoparticles inside the endosome.

2GF-GNP internalization into A431 cells was further verified by confocal microscopy (FIG. 5C i-iii) and TEM (FIG. 5C iv-v), which clearly showed accumulation of 2GF-GNP nanoparticles inside the cells.

Figure 5D:
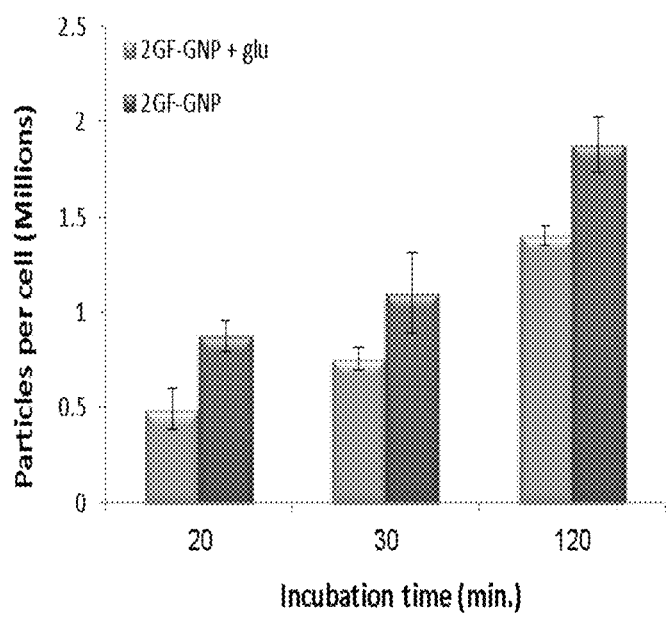
FIG. 5D is a bar graph showing results of saturation with free glucose.
Figure 5E:
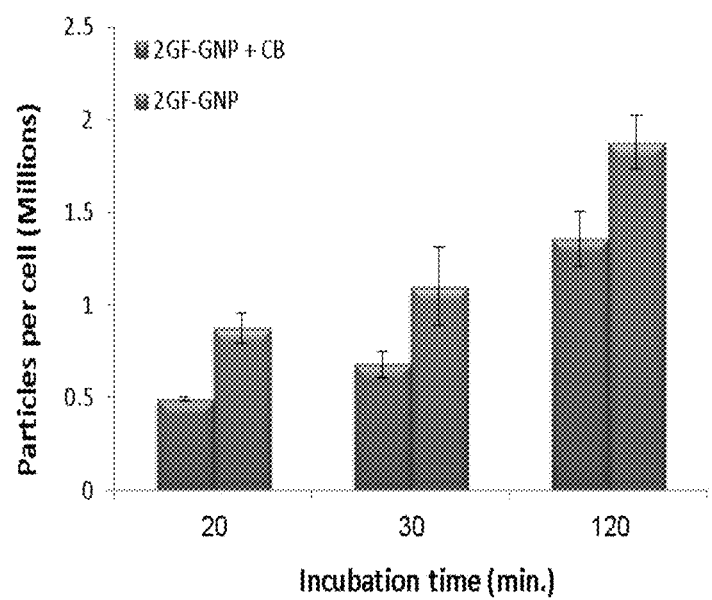
FIG. 5E is a bar graph showing results of cells uptake of 2GF-GNP in cells pre-incubated with cytochalasin B inhibitor. Results presented as mean±standard deviation (SD)
Figure 5F:
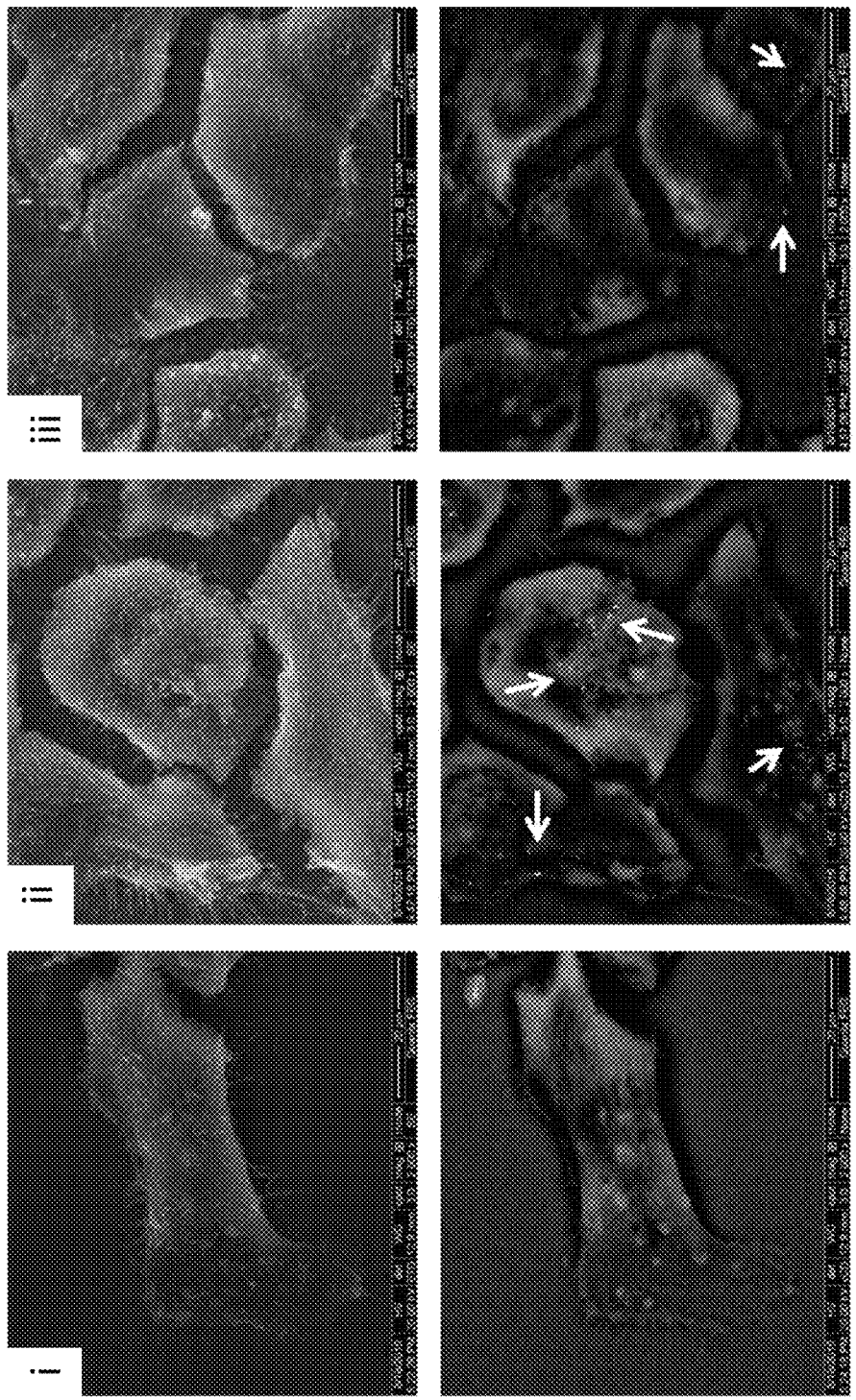
FIG. 5F shows SEM images of A431 cell surface without 2GF-GNPs (i); with 2GF-GNPs (ii); with 2GF-GNPs (iii), after preincubation with CB. Bottom images were taken in back-scattered electrons (BSE mode) with a vCD detector, gold nanoparticles are indicated by white arrows.

Focusing on GLUT-1, a competitive experiment was performed at high concentrations of glucose, which occupies and saturates GLUT-1 at the cell surface. In addition, the effect of cytochalasin B (CB), a well-known GLUT-1 inhibitor, on the cellular uptake of 2GF-GNP was examined. As demonstrated by atomic absorption spectroscopy measurements, saturation of the medium with free glucose has significantly reduced the cellular uptake of 2GF-GNP in comparison to that obtained with the lower glucose levels, at rates of 44%, 31% and 25%, after 20 minutes, 30 minutes and 120 minutes of incubation with the 2GF-GNPs, respectively (FIG. 5D). In a similar manner, pre-incubation of the cells with CB has inhibited the cellular uptake of 2GF-GNPs by 44%, 38% and 28% following same incubation times (FIG. 5E). To validate that the inhibition is not due to cytotoxicity of CB, the cellular viability following CB treatment was determined using trypan blue test, showing more than 96% viability. The observed decrease in the inhibition rates with the increasing incubation period can be attributed to non-specific internalization of the GNPs, which is more likely to occur during the long-period incubations. In addition, the cellular uptake reduction of 2GF-GNP in the presence of CB, was clearly observed by SEM images (FIG. 5Fi-iii).

Figure 5G:
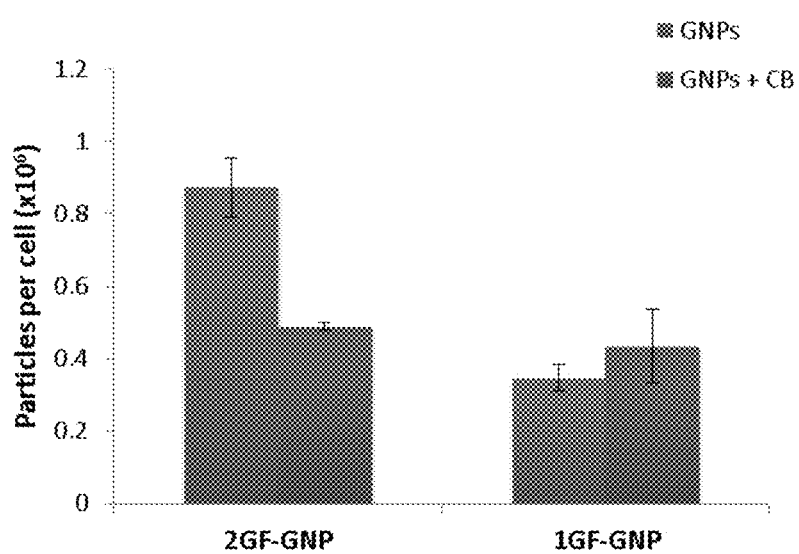
FIG. 5G is a bar graph showing results of cells uptake of 2GF-GNP in comparison to 1GF-GNP, in cells pre-incubated with cytochalasin B inhibitor. Results presented as mean±SD.

The effect of CB on the cellular uptake of 2GF-GNPs was further compared to the control particles, 1GF-GNPs. 1GF-GNP was utilized as a control, since the first carbon position in the glucose molecule interferes with the ability of the glucose transporter to recognize the glucose molecule. Thus, chemical modification on this position prevents glucose recognition by cells. Results demonstrated that while CB has significantly inhibited the cellular uptake of 2GF-GNPs, no reduction in 1GF-GNP cellular uptake has been observed after pre-incubation with CB (FIG. 5G).

Figure 6A:
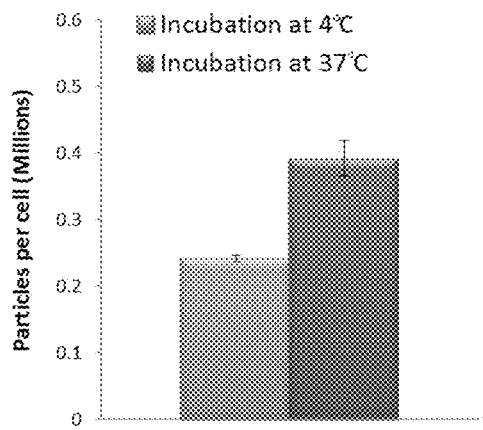
FIG. 6A-C are bar graph demonstrating 2GF-GNP uptake in 3T3 cell line following: incubation at 37° C. in comparison to 4° C. (A); saturation with free glucose (B); and Cytochalasin B inhibition test (C)
Figure 6B:
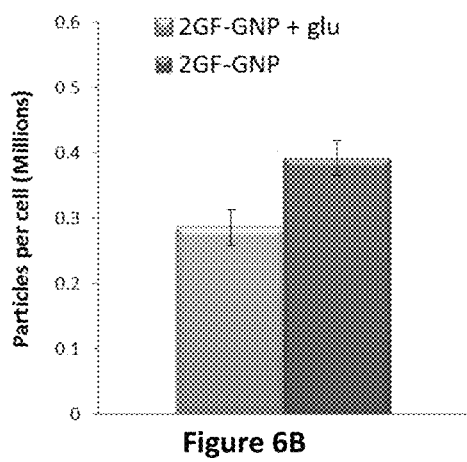
Figure 6C:
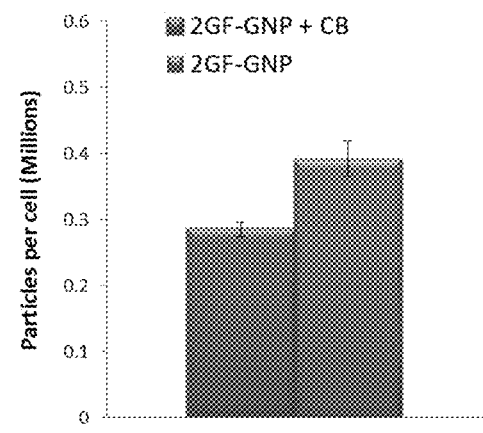

The internalization mechanism of 2GF-GNPs was further investigated using the standard fibroblast 3T3 cell line. As expected, the uptake of 2GF-GNPs in these cells was lower than in A431 cancer cells. Results of incubating 3T3 cells with 2GF-GNPs at 4° C. compared to 37° C. (FIG. 6A) as well as saturation with free glucose (FIG. 6B) and preincubation with CB (FIG. 6C), have demonstrated the same trend as in A431 cancer cells, but with lower degrees of reduction.

Altogether, these results point to a specific uptake mechanism, influenced by recognition of the glucose molecule presented at the GNPs surface by GLUT-1, which is overexpressed on the cells membrane of cancer cells such as A431 cells. The interaction between GLUT-1 and the glucose coating triggers the second step of internalization, apparently through an endocytic pathway, as demonstrated by the temperature-dependent internalization.

Example 4

Endocytosis Pathways Involved in 2GF-GNPs Uptake

To understand the next step of 2GF-GNPs internalization, after glucose recognition by GLUT-1, A431 cells were incubated with 2GF-GNPs following incubation with selective inhibitors of various endocytic pathways. Chlorpromazine was used for blocking the clathrin-dependent pathway, nystatin for blocking the caveolae-mediated endocytosis, and amiloride as an inhibitor of fluid phase pinocytosis.

Figure 7:
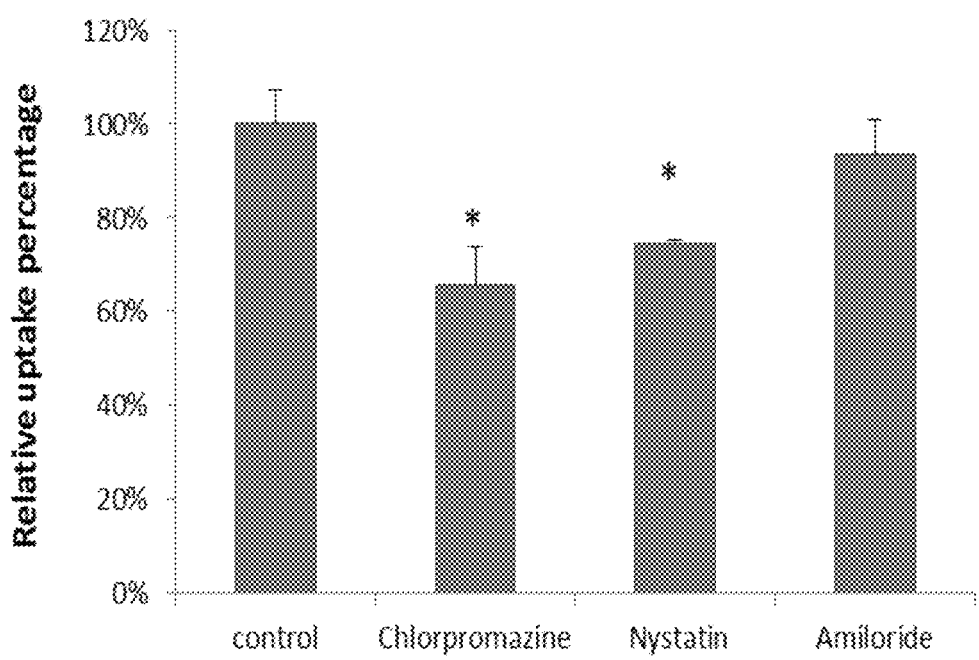
FIG. 7 is a bar graph showing results of cells uptake of 2GF-GNP in cells pre-incubated with selective inhibitors of various endocytic pathways, *p<0.05, results presented as mean±SD.

As demonstrated in FIG. 7, 2GF-GNP uptake in cells treated with chlorpromazine and nystatin was reduced by about 35% and about 25%, respectively, compared to control. In contrast, Amiloride did not affect 2GF-GNP uptake by A431 cells.

These results indicate that the two endocytic pathways clathrin-dependent pathway, and caveolae-mediated endocytosis are simultaneously involved in the 2GF-GNP uptake mechanism, while clathrin-mediated endocytosis, which is mediated by ligand-receptor recognition, is mainly involved.

Example 5

Advantageous Uptake of Gold Nanoparticles Conjugated to a Specific Glucose Derivative Via a Specific Group of Linkers In Vitro In order for glucose conjugated gold nanoparticles to serve as good contrast agents of tumor/cancer cells they should be characterized by high uptake by tumor cells and little or no aggregation in the medium in vitro. Therefore, tumor cells uptake of a variety of gold nanoparticles, each conjugated to a specific glucose derivative via a specific group of linkers, was characterized in vitro. Additionally, aggregation in the medium of these nanoparticles was also characterized. The glucose derivative used for these experiments were described above (see example 1) and different linkers used included: 2-(2-mercapto-ethoxy)-ethanol (PEG3) having a molecular weight of 122 Da, o-(2-carboxyethyl)-o-(2-mercaptoethyl) hepta ethylene glycol (PEG7) having a molecular weight of 458 Da, 4,7,10,13,16,19,22,25,32,35,38,41,44,47,50,53-Hexadecaoxa-28,29-dithia-hexapentacontanedioic acid (DPEG7) having a molecular weight of 915 Da, 12-Mercaptododecanoic acid (MDDA) having a molecular weight of 232 Da, mercapto-succinic acid (MSA) having a molecular weight of 150 Da. Human SCC A431 cells ($1 \times 10^6$) were cultured in 5 mL glucose-free DMEM medium containing 5% FCS, 0.5% Penicillin and 0.5% Glutamine. Next, the variety of examined GNPs were added and incubated with cells for 30 minutes at 37° C. Results of tumor uptake are represented as percentage (%) of a given dose, wherein low uptake is considered as a concentration of 10% of a given dose or lower (Table 1). Surprisingly, superiority of a specific group of linkers consisting of derivatives of polyethylene glycol having a molecular weight of 400-1000 Da (see table 1, for percentage of uptake by tumor cells for PEG7, D-PEG7). These derivatives did not accumulate in the medium and were found to exhibit higher uptake by tumor cells (see table 1). Furthermore, no uptake by tumor cells was demonstrated when a PEG derivative having a molecular weight of 3400 Da was used as a linker. Additionally, as further demonstrated in table 1, gold nanoparticles conjugated to 2 deoxy-D-glucose through its 2' carbon position (denoted as 2GF) exhibit higher uptake by tumor/cancer cells, strengthening the findings described in Example 1.

TABLE 1

In vitro results of tumor cells uptake of different
types of glucose conjugated gold nanoparticle

|     |                       | PEG3 | PEG7 | MSA  | MDDA | D-PEG7 |
|-----|-----------------------|------|------|------|------|--------|
| 1GF | Aggregations in medium | NO   | NO   | NO   | Yes  | NO     |
|     | uptake by Tumor cells  | 6%   | 5.5% | 4.2% | 18%  | 4%     |
| 2GF | Aggregations in medium | NO   | NO   | NO   | Yes  | NO     |
|     | uptake by Tumor cells  | 6%   | 30%  | 2.5% | 25%  | 28%    |
| 3GF | Aggregations in medium | NO   | NO   | NO   | Yes  | NO     |
|     | uptake by Tumor cells  | 10%  | 11%  | 0.8% | 12%  | 10%    |
| 6GF | Aggregations in medium | NO   | NO   | NO   | Yes  | NO     |
|     | uptake by Tumor cells  | 6.4% | 10%  | 2.4% | 8%   | 9%     |

Example 6

Advantageous Uptake of Gold Nanoparticles Conjugated to a Specific Glucose Derivative Via a Specific Group of Linkers In Vivo Some of the glucose conjugated gold nanoparticles including: o-(2-carboxyethyl)-o-(2-mercaptoethyl) hepta ethylene glycol (PEG7) having a molecular weight of 458 Da, Poly(ethylene glycol) 2-mercaptoethyl ether acetic acid (PEG1000) having a molecular weight of 1000 Da and 12-Mercaptododecanoic acid (MDDA) having a molecular weight of 232 Da were further examined in vivo, in order to find which are characterized by high uptake by tumor cells in vivo and do not cause pulmonary embolism. For in vivo experiments, A431 cells ($2 \times 10^6$) were injected subcutaneously into the back flank area of nude mice aged 6 weeks. When the tumor reached a diameter of 4-5 mm, the variety of GF-GNPs (200 μL, 30 mg/mL) were intravenously injected into their tail vein. Experimental procedure was identical for all GF-GNP. Gold concentration in the tumor was quantitatively measured by atomic absorption spectroscopy at 3.5 h post intravenous (IV) injection. Low concentration is considered as a concentration of 3% of injected dose or lower. Additionally, blood circulation time of theses glucose conjugated gold nanoparticles was measured. Results are summarized in table 2. These results further support the superiority of gold nanoparticles conjugated to 2 deoxy-d-glucose through its 2' carbon position via a specific group of linkers consisting of derivatives of polyethylene glycol having a molecular weight of 458-1000 Da.

TABLE 2

In vivo results of tumor uptake of different types
of glucose conjugated gold nanoparticle

|     |                          | PEG7   | MDDA    | PEG1000 |
|-----|--------------------------|--------|---------|---------|
| 1GF | pulmonary embolism       | NO     | NO      | NO      |
|     | uptake by Tumor          | 2% ID  | 0.2% ID | N.D     |
|     | blood circulation (hours)| <2 hr  | <2 hr   | N.D     |
| 2GF | pulmonary embolism       | NO     | NO      | NO      |
|     | uptake by Tumor          | 8%     | 3% ID   | 25% ID  |
|     | blood circulation (hours)| <2 hr  | <2 hr   | >>2 hr  |
| 3GF | pulmonary embolism       | NO     | NO      | N.D     |
|     | uptake by Tumor          | 1.5% ID| 0.3% ID | N.D     |
|     | blood circulation (hours)| <2 hr  | <2 hr   | N.D     |
| 6GF | pulmonary embolism       | NO     | NO      | N.D     |
|     | uptake by Tumor          | 1.6% ID| 0.1% ID | N.D     |
|     | blood circulation (hours)| <2 hr  | <2 hr   | N.D     |

ID = injected dose,
N.D = no data

What is claimed is:

1. A composition comprising:
   a gold nanoparticle;
   PEG or derivatives thereof, wherein said PEG and derivatives thereof have a molecular weight of 400 to 1000 Dalton; and
   a 2-Deoxy-D-glucose,
   wherein said PEG or derivatives thereof are linked to said gold nanoparticle and to said 2-Deoxy-D-Glucose, wherein said PEG or derivatives thereof are linked to said gold nanoparticle via a chemical attachment selected from the group consisting of: covalent attachment, semi-covalent attachment and non-covalent attachment,
   wherein said 2-Deoxy-D-Glucose is linked to said PEG and derivatives thereof at the 2-Carbon position of said 2-Deoxy-D-Glucose; and
   wherein said composition has a diameter of 20 to 60 nanometers.

2. The composition of claim 1, wherein said gold has a concentration of 30 to 60 milligrams/milliliter.

3. The composition of claim 1, wherein said 2-Deoxy-D-Glucose is covalently linked to said PEG.

4. The composition of claim 1, wherein said PEG or derivatives thereof comprise one or more functional groups selected from the group consisting of: mercapto group, carboxyl group, mercaptoethyl, carboxyethyl, hydroxyl, amine, imide, sulfone, disulfide, and NHS esters.

5. The composition of claim 1, wherein said gold nanoparticle is linked to 4,000-20,000 molecules of said PEG or derivative thereof.

6. The composition of claim 1, wherein said gold nanoparticle is linked to 4,000-20,000 molecules of said 2-deoxy-D-glucose.

7. The composition of claim 1, wherein said gold nanoparticle has a diameter of 10 to 40 nanometers.

8. The composition of claim 1, further comprising a drug.

9. The composition of claim 8, wherein said drug is an anti-cancer therapeutic agent.

10. A method of imaging a tumor comprising:
    administering to a subject the composition of claim 1, allowing said composition to penetrate and accumulate in tumor cells; and
    scanning said subject or a portion thereof using a diagnostic imaging technique, thereby imaging said tumor cells.

11. The method of claim 10, wherein said diagnostic imaging technique is selected from the group consisting: computed X-ray tomography (CT), ultrasound (US) and magnetic resonance imaging (MM).

12. The method of claim 10, wherein said administering is by an intravenous injection.

13. The method of claim 10, wherein said scanning is performed 0.5 to 24 hours post said administering.

14. The method of claim 10, wherein said subject is a human subject.

15. The method of claim 10, wherein said subject is at risk of being afflicted with cancer.

16. The method of claim 10, wherein said drug is an anti-cancer therapeutic agent.

17. The method of claim 16, wherein said drug is activated within said tumor cells.

18. The method of claim 10, further comprising a step of directing an ionizing irradiation to the composition thereby obtaining locally enhanced radiation therapy within said tumor cells.

* * * * *